United States Patent
Hester, II et al.

(10) Patent No.: US 9,266,861 B2
(45) Date of Patent: Feb. 23, 2016

(54) METHOD OF SYNTHESIZING THYROID HORMONE ANALOGS AND POLYMORPHS THEREOF

(71) Applicants: Madrigal Pharmaceuticals, Inc., Fort Washington, PA (US); Hoffmann-La Roche Inc., Nutley, NJ (US)

(72) Inventors: D. Keith Hester, II, Delmar, NY (US); Robert J. Duguid, Glenmont, NY (US); Martha J. Kelly, Collegeville, PA (US); Anna Chasnoff, Altamont, NY (US); Gang Dong, Schenectady, NY (US); Edwin L. Crow, Santa Fe, NM (US); Duk Soon Choi, Flanders, NJ (US); Lianhe Shu, Livingston, NJ (US); Ping Wang, Nutley, NJ (US)

(73) Assignees: Madrigal Pharmaceuticals, Inc., Fort Washington, PA (US); Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 14/660,720

(22) Filed: Mar. 17, 2015

(65) Prior Publication Data

US 2015/0203473 A1    Jul. 23, 2015

Related U.S. Application Data

(63) Continuation of application No. PCT/US2013/060177, filed on Sep. 17, 2013.

(60) Provisional application No. 61/790,432, filed on Mar. 15, 2013, provisional application No. 61/702,137, filed on Sep. 17, 2012.

(51) Int. Cl.
| | |
|---|---|
| *C07D 403/12* | (2006.01) |
| *C07D 403/02* | (2006.01) |
| *C07D 237/16* | (2006.01) |
| *A61K 31/53* | (2006.01) |
| *A61K 31/50* | (2006.01) |

(52) U.S. Cl.
CPC ............ *C07D 403/12* (2013.01); *A61K 31/50* (2013.01); *A61K 31/53* (2013.01); *C07D 237/16* (2013.01); *C07B 2200/13* (2013.01)

(58) Field of Classification Search
CPC ............. C07D 253/075; C07D 237/14; C07D 403/10; C07D 237/16; C07D 403/12; A61K 31/53
USPC ................................... 544/182, 240; 514/242
See application file for complete search history.

(56) References Cited

U.S. PATENT DOCUMENTS

| | | | |
|---|---|---|---|
| 7,452,882 B2 | 11/2008 | Haynes et al. | |
| 7,807,647 B2 | 10/2010 | Sheikhnejad et al. | |
| 7,807,674 B2 | 10/2010 | Haynes et al. | |
| 8,076,334 B2 | 12/2011 | Haynes et al. | |

FOREIGN PATENT DOCUMENTS

| | | |
|---|---|---|
| WO | WO 2007-009913 A1 | 1/2007 |
| WO | WO 2009-037172 A1 | 3/2009 |

OTHER PUBLICATIONS

M. Adams, et al., "Genetic Analysis of 29 Kindreds with Generalized and Pituitary Resistance to Thyroid Hormone Identification of Thirteen Novel Mutations in the Thyroid Hormone Receptor β Gene," J. Clin. Invest. 94:506-515 (1994).
Deirdre M. B. Hickey et al., "Synthesis of Thyroid Hormone Analogues. 1-51 Part 3. Iodonium Salt Approaches to SK&F L-94901," J. Chem. Soc., Perkin Trans. 1, pp. 3103-3111 (1988) Abstract, 1 page.
B. R. Huber et al., "Thyroid Hormone Receptor-β Mutations Conferring Hormone Resistance and Reduced Corepressor Release Exhibit Decreased Stability in the N-terminal Ligand-Binding Domain," Molecular Endocrinology 17(1):107-116 (2003).
B. R. Huber et al., "Two Resistance to Thyroid Hormone Mutants with Impaired Hormone Binding" Molecular Endocrinology 17(4):643-652 (2003).
A. Joharapurkar et al., "Selective Thyromimetics Using Receptor and Tissue Selectivity Approaches: Prospects for Dyslipidemia," J. Med. Chem. 55 (12): 5649-5675 (2012).
R. Wagner et al., "Hormone Selectivity in Thyroid Hormone Receptors," Molecular Endocrinology 15(3): 398-410 (2001).

*Primary Examiner* — Venkataraman Balasubramanian
(74) *Attorney, Agent, or Firm* — Cooley LLP; Heidi A. Erlacher; Lian Ouyang

(57) ABSTRACT

The disclosure describes methods of synthesis of pyridazinone compounds as thyroid hormone analogs and their prodrugs. Preferred methods according to the disclosure allow for large-scale preparation of pyridazinone compounds having high purity. In some embodiments, preferred methods according to the disclosure also allow for the preparation of pyridazinone compounds in better yield than previously used methods for preparing such compounds. Also disclosed are morphic forms of a pyridazinone compound. Further disclosed is a method for treating resistance to thyroid hormone in a subject having at least one TRβ mutation.

17 Claims, 9 Drawing Sheets

METHOD OF SYNTHESIZING THYROID HORMONE ANALOGS AND POLYMORPHS THEREOF

RELATED APPLICATIONS

This application is a continuation application of International Application PCT/US2013/060177 with an international filing date of Sep. 17, 2013, which claims priority to, and the benefit of, U.S. provisional application No. 61/702,137, filed Sep. 17, 2012 and U.S. provisional application No. 61/790,432, filed Mar. 15, 2013, the entire contents of each of which are incorporated herein by reference in their entireties.

INCORPORATION-BY-REFERENCE OF SEQUENCE LISTING

The contents of the text file named "41245-522001WO_ST25.txt", which was created on Sep. 16, 2013 and is 4 KB in size, are hereby incorporated by reference in their entirety.

BACKGROUND

Thyroid hormones are critical for normal growth and development and for maintaining metabolic homeostasis (Paul M. Yen, Physiological reviews, Vol. 81(3): pp. 1097-1126 (2001)). Circulating levels of thyroid hormones are tightly regulated by feedback mechanisms in the hypothalamus/pituitary/thyroid (HPT) axis. Thyroid dysfunction leading to hypothyroidism or hyperthyroidism clearly demonstrates that thyroid hormones exert profound effects on cardiac function, body weight, metabolism, metabolic rate, body temperature, cholesterol, bone, muscle and behavior.

The biological activity of thyroid hormones is mediated by thyroid hormone receptors (TRs or THRs) (M. A. Lazar, Endocrine Reviews, Vol. 14: pp. 348-399 (1993)). TRs belong to the superfamily known as nuclear receptors. TRs form heterodimers with the retinoid receptor that act as ligand-inducible transcription factors. TRs have a ligand binding domain, a DNA binding domain, and an amino terminal domain, and regulate gene expression through interactions with DNA response elements and with various nuclear co-activators and co-repressors. The thyroid hormone receptors are derived from two separate genes, α and β. These distinct gene products produce multiple forms of their respective receptors through differential RNA processing. The major thyroid receptor isoforms are α1, α2, β1 and β2. Thyroid hormone receptors α1, β1 and β2 bind thyroid hormone. It has been shown that the thyroid hormone receptor subtypes can differ in their contribution to particular biological responses. Recent studies suggest that TRβ1 plays an important role in regulating TRH (thyrotropin releasing hormone) and on regulating thyroid hormone actions in the liver. TRβ2 plays an important role in the regulation of TSH (thyroid stimulating hormone) (Abel et. al., J. Clin. Invest., Vol 104: pp. 291-300 (1999)). TRβ1 plays an important role in regulating heart rate (B. Gloss et. al. Endocrinology, Vol. 142: pp. 544-550 (2001); C. Johansson et. al., Am. J. Physiol., Vol. 275: pp. R640-R646 (1998)).

Efforts have been made to synthesize thyroid hormone analogs which exhibit increased thyroid hormone receptor beta selectivity and/or tissue selective action. Such thyroid hormone mimetics may yield desirable reductions in body weight, lipids, cholesterol, and lipoproteins, with reduced impact on cardiovascular function or normal function of the hypothalamus/pituitary/thyroid axis (see, e.g., Joharapurkar et al., J. Med. Chem., 2012, 55 (12), pp 5649-5675). The development of thyroid hormone analogs which avoid the undesirable effects of hyperthyroidism and hypothyroidism while maintaining the beneficial effects of thyroid hormones would open new avenues of treatment for patients with metabolic disease such as obesity, hyperlipidemia, hypercholesterolemia, diabetes and other disorders and diseases such as liver steatosis and NASH, atherosclerosis, cardiovascular diseases, hypothyroidism, thyroid cancer, thyroid diseases, resistance to thyroid hormone and related disorders and diseases.

The present invention, in part, provides methods for synthesizing thyroid hormone analogs such as pyridazinone compounds and prodrugs thereof. An ideal method of synthesizing the thyroid hormone analogs and their prodrugs would, for example, provide product compounds in high purity and high yield. The present invention is directed at providing one or more of these desirable features.

SUMMARY OF THE DISCLOSURE

The present disclosure describes a synthetic process, which may be used to prepare 6-(4-amino-2,6-dichlorophenoxy)-4-isopropylpyridazin-3(2H)-one ("Int. 7"), a compound that is useful as an intermediate for making pyridazinone compounds as thyroid hormone analogs, as follows:

(a) contacting $R^1MgX$ or $R^1Li$ with a compound of Formula (I):

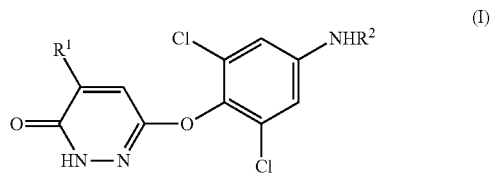

to form a compound of Formula (II):

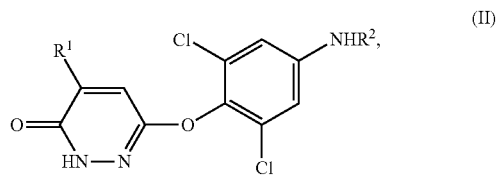

in which $R^1$ is isopropyl or isopropenyl, X is halo and $R^2$ is H or an amine protecting group; and (b) converting the compound of Formula (II) to a compound of Formula (III):

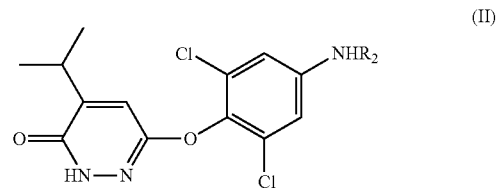

in the presence of a base when $R^1$ is isopropenyl or in the presence of an oxidizing agent when $R^1$ is isopropyl.

In step (a), the solvent can be an aprotic organic solvent, such as THF, diethyl ether, toluene, or dioxane, the reaction temperature can be 0-60° C., 20-50° C., 30-45° C., or 35-45° C., the reaction time can be 10 min to 10 hours, 1-8 hours, or 3-5 hours, and the amount of the Grignard reagent (R¹MgX) can be 3-10 equivalents or 3-6 equivalents of the compound of Formula (I).

In step (b), the base is used to isomerize the compound of Formula (II). It can be an organic base or an inorganic base. Examples of bases include, but are not limited to, triethylamine, pyridine, KOH, NaOH, and carbonates. The isomerization can also be achieved under other conditions, e.g., treatment with an acid or heating in an aprotic solvent.

Also, in step (b), the oxidizing agent is not particularly limited. For example, one can use bromine in acetic acid or propionic acid.

Examples of amine protecting groups include, but are not limited to, substituted alkyl, acyl (e.g., benzoyl or acetyl) and silyl. Hydroxy and amine protecting groups have been discussed in T. W. Greene and P. G. M. Wuts, Protective Groups in Organic Synthesis, 2d. Ed., John Wiley and Sons (1991).

In one embodiment, step (a) is performed by contacting R¹MgX with the compound of Formula (I), in which R¹ is isopropenyl and X is Br. The solvent used in this reaction can be THF with a volume to weight ratio of THF to the compound of Formula (I) ranging between 7 and 30 (or between 7 and 15). This step may be performed in the presence of a Lewis acid (e.g., a lithium halide).

In one embodiment, step (a) is performed by contacting R¹MgX with the compound of Formula (I), in which R¹ is isopropyl and X is Cl. The solvent used in this reaction can be THF with a volume to weight ratio of THF to the compound of Formula (I) ranging between 7 and 30 (or between 7 and 15). This step may be performed in the presence of a Lewis acid (e.g., a lithium halide).

In one embodiment, the base in step (b) is a metal hydroxide (e.g., potassium hydroxide).

In one embodiment, the oxidizing agent in step (b) is bromine and step (b) is performed in the presence of an acid.

In one embodiment, the R² group in Formula (I) and Formula (II) is acetyl or benzoyl. In a further embodiment, R² is benzoyl.

In one embodiment, the process further comprises providing the compound of Formula (I) by contacting 3,6-dichloropyridazine with 2,6-dichloro-4-aminophenol to form 3,5-dichloro-4-((6-chloropyridazin-3-yl)oxy)aniline, hydrolyzing 3,5-dichloro-4-((6-chloropyridazin-3-yl)oxy) aniline and protecting the amine group of 3,5-dichloro-4-((6-chloropyridazin-3-yl)oxy)aniline either before or after the hydrolysis to form the compound of Formula (I). The contacting of 3,6-dichloropyridazine with 2,6-dichloro-4-aminophenol is performed in a polar aprotic solvent (e.g., dimethylacetamide (DMAC)) in the presence of a base (e.g., Cs₂CO₃) at a reaction temperature between 60 and 120° C. (e.g., about 65° C.). Further, a purification step may be included. That is, before step (a), the compound of Formula (I) is purified in an acidic solution at a temperature between 80 and 100° C.

In one embodiment, the process further comprises step (c) when present, removing the amine protecting group R² of the compound of Formula (III) to form 6-(4-amino-2,6-dichlorophenoxy)-4-isopropylpyridazin-3(2H)-one.

In one embodiment, the compound, e.g., Int. 7, made by the method described herein has a purity of greater than 85%, e.g., greater than 86%, greater than 90%, greater than 92.5%, greater than 95%, greater than 96%, greater than 97%, greater than 97.5%, greater than 98%, greater than 98.5%, greater than 99%, greater than 99.2%, greater than 99.5%, or greater than 99.8%.

In one embodiment, the compound, i.e., 6-(4-amino-2,6-dichlorophenoxy)-4-isopropylpyridazin-3(2H)-one, made by the method described herein has less than 1.5% of 6-(4-amino-2,6-dichlorophenoxy)-5-isopropylpyridazin-3(2H)-one, e.g., less than 1.0% of 6-(4-amino-2,6-dichlorophenoxy)-5-isopropylpyridazin-3(2H)-one, or less than 0.5% of 6-(4-amino-2,6-dichlorophenoxy)-5-isopropylpyridazin-3 (2H)-one.

In another embodiment, the compound made by the above-described process is free of 6-(4-amino-2,6-dichlorophenoxy)-5-isopropylpyridazin-3(2H)-one.

The synthetic process of this invention may further comprise the following step to synthesize pyridazinone compounds as thyroid hormone analogs and their prodrugs:

(d) converting 6-(4-amino-2,6-dichlorophenoxy)-4-isopropylpyridazin-3(2H)-one to the compound of Formula (IV):

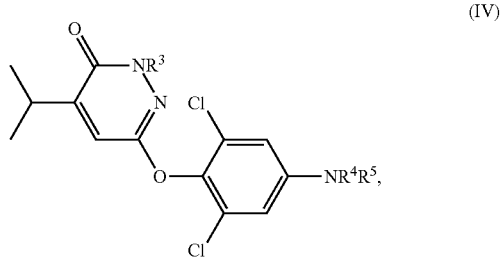

(IV)

wherein

R³ is H or CH₂R_a, in which R_a is hydroxyl, O-linked amino acid, —OP(O)(OH)₂ or —OC(O)—R_b, R_b being lower alkyl, alkoxy, alkyl acid, cycloalkyl, aryl, heteroaryl, or —(CH₂)_n-heteroaryl and n being 0 or 1;

R⁴ is H, and R⁵ is CH₂COOH, C(O)CO₂H, or an ester or amide thereof, or R⁴ and R⁵ together are —N=C(R_c)—C(O)—NH—C(O)—; in which R_c is H or cyano.

In one embodiment, the compound of Formula (IV) is 2-(3,5-dichloro-4-((5-isopropyl-6-oxo-1,6-dihydropyridazin-3-yl)oxy)phenyl)-3,5-dioxo-2,3,4,5-tetrahydro-1,2,4-triazine-6-carbonitrile ("Compound A") and the above step is performed by contacting 6-(4-amino-2,6-dichlorophenoxy)-4-isopropylpyridazin-3(2H)-one with ethyl (2-cyanoacetyl)carbamate and a metal nitrite followed by treatment with potassium acetate in DMAC.

In one embodiment, the process further comprises forming a morphic form of 2-(3,5-dichloro-4-((5-isopropyl-6-oxo-1,6-dihydropyridazin-3-yl)oxy)phenyl)-3,5-dioxo-2,3,4,5-tetrahydro-1,2,4-triazine-6-carbonitrile ("Compound A") (Form I) characterized by an X-ray powder diffraction pattern including peaks at about 10.5, 18.7, 22.9, 23.6, and 24.7 degrees 2θ.

In one embodiment, the compound of Formula (IV) is of Formula (V)

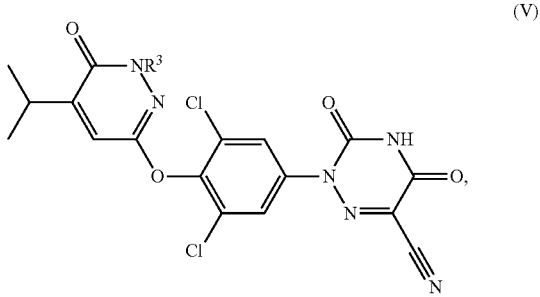

(V)

wherein $R^3$ is $CH_2R_a$, and step (d) is performed by contacting 6-(4-amino-2,6-dichlorophenoxy)-4-isopropylpyridazin-3(2H)-one with ethyl (2-cyanoacetyl)carbamate followed by treatment with potassium acetate in DMAC to form 2-(3,5-dichloro-4-((5-isopropyl-6-oxo-1,6-dihydropyridazin-3-yl)oxy)phenyl)-3,5-dioxo-2,3,4,5-tetrahydro-1,2,4-triazine-6-carbonitrile ("Compound A") and converting Compound A to the compound of Formula (V) in a suitable manner, e.g., using one of the techniques described in U.S. Pat. No. 8,076,334.

In one embodiment, the compound of Formula (IV), e.g., 2-(3,5-dichloro-4-((5-isopropyl-6-oxo-1,6-dihydropyridazin-3-yl)oxy)phenyl)-3,5-dioxo-2,3,4,5-tetrahydro-1,2,4-triazine-6-carbonitrile ("Compound A"), made by the method described herein has a purity of greater than 85%, e.g., greater than 86%, greater than 90%, greater than 92.5%, greater than 95%, greater than 96%, greater than 97%, greater than 97.5%, greater than 98%, greater than 98.5%, greater than 99%, greater than 99.2%, greater than 99.5%, or greater than 99.8%. For example, the content of impurities (i.e., any components of the composition produced by the method described herein, other than compound of Formula (IV), such as byproducts, starting material, solvent residues, heavy metal, and etc.) is less than 15%, less than 14%, less than 10%, less than 8%, less than 5%, less than 4%, less than 3%, less than 2%, less than 1.5%, less than 1%, less than 0.8%, less than 0.5%, or less than 0.2%.

In one embodiment, the compound of Formula (IV) made by the method described herein is Compound A in Form I, and has a purity of greater than 85%, e.g., greater than 86%, greater than 90%, greater than 92.5%, greater than 95%, greater than 96%, greater than 97%, greater than 97.5%, greater than 98%, greater than 98.5%, greater than 99%, greater than 99.2%, greater than 99.5%, or greater than 99.8%. For example, the content of impurities (i.e., any components of the composition produced by the method described herein, other than Compound A, such as byproducts, starting material, solvent residues, heavy metal, and etc.) is less than 15%, less than 14%, less than 10%, less than 8%, less than 5%, less than 4%, less than 3%, less than 2%, less than 1.5%, less than 1%, less than 0.8%, less than 0.5%, or less than 0.2%.

In one embodiment, the compound of Formula (IV) made by the method described herein is Compound A in Form I, and Form I has a purity of greater than 85%, e.g., greater than 86%, greater than 90%, greater than 92.5%, greater than 95%, greater than 96%, greater than 97%, greater than 97.5%, greater than 98%, greater than 98.5%, greater than 99%, greater than 99.2%, greater than 99.5%, or greater than 99.8%. For example, the content of impurities (i.e., any components of the composition produced by the method described herein, other than Form I, such as other morphic forms of Compound A, byproducts, starting material, solvent residues, heavy metal, and etc.) is less than 15%, less than 14%, less than 10%, less than 8%, less than 5%, less than 4%, less than 3%, less than 2%, less than 1.5%, less than 1%, less than 0.8%, less than 0.5%, or less than 0.2%.

In one embodiment, the composition comprising a compound of Formula (IV), such as Compound A, made by the method described herein, has less than 1.5% (e.g., less than 1.0%, e.g., less than 0.5%) of the corresponding β-isopropylpyridazin-3(2H)-one regioisomer (e.g., 2-(3,5-dichloro-4-(4-isopropyl-6-oxo-1,6-dihydropyridazin-3-yl)oxy)phenyl)-3,5-dioxo-2,3,4,5-tetrahydro-1,2,4-triazine-6-carbonitrile, the β-isopropylpyridazin-3(2H)-one regioisomer of Compound A).

In one embodiment, the composition comprising a compound of Formula (IV), such as Compound A, made by the method described herein is free of the corresponding β-isopropylpyridazin-3(2H)-one regioisomer (e.g., 2-(3,5-dichloro-4-(4-isopropyl-6-oxo-1,6-dihydropyridazin-3-yl)oxy)phenyl)-3,5-dioxo-2,3,4,5-tetrahydro-1,2,4-triazine-6-carbonitrile, the β-isopropylpyridazin-3(2H)-one regioisomer of Compound A).

In one embodiment, the composition comprising a compound of Formula (IV), such as Compound A, made by the method described herein has less than 1.5% (e.g., less than 0.1%) of heavy metal, e.g., silver.

In one embodiment, the composition comprising a compound of Formula (IV), such as Compound A, made by the method described herein is free of heavy metal, e.g., silver, gold, or platinum.

The synthetic methods described herein include advantages compared to the previous methods, such as those disclosed in U.S. Pat. No. 7,452,882. For example, the overall yield of 2-(3,5-dichloro-4-(5-isopropyl-6-oxo-1,6-dihydropyridazin-3-yl)oxy)phenyl)-3,5-dioxo-2,3,4,5-tetrahydro-1,2,4-triazine-6-carbonitrile ("Compound A") is greatly increased (e.g., >40% versus ~9% when made according to the method disclosed in U.S. Pat. No. 7,452,882). Also, regioselectivity of the synthesis is far superior. Further, the new methods offer easier processing, e.g., easier filtrations. Lastly, no heavy metals are used in the methods described herein for Compound A. In comparison, silver was used in the route described in U.S. Pat. No. 7,452,882, which necessitated remediation treatment with a resin.

In yet another aspect, the invention features a composition comprising greater than 85% of a compound of Formula (IV), less than 1.5% of the corresponding β-isopropylpyridazin-3(2H)-one regioisomer (i.e.,

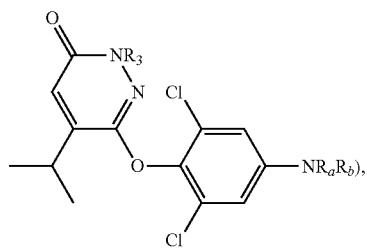

and/or has less than 1.5% of heavy metal.

In one embodiment, the compound of Formula (IV), e.g., Compound A, has a purity of greater than 85%, e.g., greater than 86%, greater than 90%, greater than 92.5%, greater than 95%, greater than 96%, greater than 97%, greater than 97.5%, greater than 98%, greater than 98.5%, greater than 99%, greater than 99.2%, greater than 99.5%, or greater than 99.8%. For example, the content of impurities (i.e., any components of a composition comprising the compound of Formula (IV), other than the compound of Formula (IV), such as byproducts, starting material, solvent residues, heavy metal, and etc.) is less than 15%, less than 14%, less than 10%, less than 8%, less than 5%, less than 4%, less than 3%, less than 2%, less than 1.5%, less than 1%, less than 0.8%, less than 0.5%, or less than 0.2%.

In one embodiment, the compound of Formula (IV) is Compound A in Form I, and has a purity of greater than 85%, e.g., greater than 86%, greater than 90%, greater than 92.5%, greater than 95%, greater than 96%, greater than 97%, greater than 97.5%, greater than 98%, greater than 98.5%, greater than 99%, greater than 99.2%, greater than 99.5%, or greater than 99.8%. For example, the content of impurities (i.e., any components of a composition comprising Compound A, other than Compound A, such as byproducts, starting material, solvent residues, heavy metal, and etc.) is less than 15%, less than 14%, less than 10%, less than 8%, less than 5%, less than 4%, less than 3%, less than 2%, less than 1.5%, less than 1%, less than 0.8%, less than 0.5%, or less than 0.2%.

In one embodiment, the compound of Formula (IV) is Compound A in Form I, and Form I has a purity of greater than 85%, e.g., greater than 86%, greater than 90%, greater than 92.5%, greater than 95%, greater than 96%, greater than 97%, greater than 97.5%, greater than 98%, greater than 98.5%, greater than 99%, greater than 99.2%, greater than 99.5%, or greater than 99.8%. For example, the content of impurities (i.e., any components of a composition comprising Form I, other than Form I, such as other morphic forms of Compound A, byproducts, starting material, solvent residues, heavy metal, and etc.) is less than 15%, less than 14%, less than 10%, less than 8%, less than 5%, less than 4%, less than 3%, less than 2%, less than 1.5%, less than 1%, less than 0.8%, less than 0.5%, or less than 0.2%.

In one embodiment, the compound of Formula (IV), such as Compound A, has less than 1.5% (e.g., less than 1.0%, e.g., less than 0.5%) of the corresponding β-isopropylpyridazin-3 (2H)-one regioisomer (e.g., 2-(3,5-dichloro-4-((4-isopropyl-6-oxo-1,6-dihydropyridazin-3-yl)oxy)phenyl)-3,5-dioxo-2, 3,4,5-tetrahydro-1,2,4-triazine-6-carbonitrile, the β-isopropylpyridazin-3(2H)-one regioisomer of Compound A).

In one embodiment, the compound of Formula (IV), such as Compound A, is free of the corresponding β-isopropylpyridazin-3(2H)-one regioisomer (e.g., 2-(3,5-dichloro-4-((4-isopropyl-6-oxo-1,6-dihydropyridazin-3-yl)oxy)phenyl)-3, 5-dioxo-2,3,4,5-tetrahydro-1,2,4-triazine-6-carbonitrile, the β-isopropylpyridazin-3(2H)-one regioisomer of Compound A).

In one embodiment, the compound of Formula (IV), such as Compound A, has less than 1.5% (e.g., less than 1.0%, e.g., less than 0.5%) of heavy metal, e.g., silver, gold, or platinum.

In one embodiment, the compound of Formula (IV), such as Compound A, made by the method described herein is free of heavy metal, e.g., silver.

Further, the invention features a morphic form of 2-(3,5-dichloro-4-((5-isopropyl-6-oxo-1,6-dihydropyridazin-3-yl) oxy)phenyl)-3,5-dioxo-2,3,4,5-tetrahydro-1,2,4-triazine-6-carbonitrile ("Compound A") (Form I) characterized by an X-ray powder diffraction ("XRPD") pattern including peaks at about 10.5, 18.7, 22.9, 23.6, and 24.7 degrees 2θ.

In one embodiment, Form I is characterized by an X-ray powder diffraction pattern further including peaks at about 8.2, 11.2, 15.7 16.4, 17.7, 30.0, and 32.2 degrees 2θ.

In one embodiment, Form I is characterized by an X-ray powder diffraction pattern including peaks at about 8.2, 10.5, 18.7, 22.9, 23.6, and 24.7 degrees 2θ.

In one embodiment, Form I is characterized by an X-ray powder diffraction pattern including peaks at about 8.2, 10.5, 11.2, 15.7 16.4, 17.7, 18.7, 22.9, 23.6, and 24.7 degrees 2θ.

In one embodiment, Form I is characterized by an X-ray powder diffraction pattern including peaks at about 8.2, 10.5, 11.2, 15.7 16.4, 17.7, 18.7, 22.9, 23.6, 24.7, 30.0, and 32.2 degrees 2θ.

In another embedment, Form I is characterized by an X-ray powder diffraction pattern substantially similar to that set forth in FIG. 1.

In another aspect, the present disclosure describes a process of preparing Form I. The process comprises mixing a sample containing Compound A (e.g., either crude or purified preparation of Compound A) with an organic solvent, such as alcohol (e.g., ethanol), ketone (e.g., methyl isobutyl ketone, i.e., MIBK), or an aqueous solution including alcohol or ketone. For example, the resulting mixture (e.g., a slurry or suspension) containing the staring Compound A and the solvent is heated at a first temperature, and then cooled to a second temperature that is lower than the first temperature. Preferably, the organic solvent is ethanol. The starting Compound A which goes into the form conversion can be a solvate, such as a hydrate (e.g., a monohydrate or dihydrate), or a solvate of an organic solvent (for example dimethyl acetamide, ethanol or MIBK). Alternatively, the starting Compound A can be an ansolvate (e.g., an anhydrate).

In one embodiment, the process is performed by heating the Compound A with the organic solvent to an elevated temperature (e.g., about 60-110° C. or about 80° C.) to form a slurry or suspension, followed by cooling (e.g., to a temperature about 0-60° C., about 40-60° C., about 45-55° C., or at about room temperature) to give Compound A Form I. For example, the organic solvent is ethanol and slurry containing Compound A can be cooled to a temperature greater than about 40° C. to obtain Form I. For example, the organic solvent is MIBK, and slurry containing Compound A can be cooled to room temperature to obtain Form I.

In another embodiment, an ethanol suspension of Compound A is heated to an elevated temperature (e.g., about 80° C.) and then cooled to a temperature not lower than about 40° C. (e.g., about 45-55° C.), filtered (e.g., about 45-55° C.), washed with warmed (e.g., 45-55° C.) ethanol and dried at e.g., 45-55° C. to obtain Form I of Compound A that is substantially free of any solvate of Compound A such as ethanol solvate. For example, Form I of Compound A as prepared has ethanol solvate content of <5% (e.g., <2%, <1%, <0.5%, or <0.1%).

In one embodiment, the process further comprises, after cooling the mixture, filtering the mixture. The filtration step can be performed at a temperature between about 0° C. and about 60° C. (e.g., about 40-60° C., about 45-55° C., or at about room temperature) to obtain a filter cake.

In one embodiment, the process further comprises, after filtering the mixture, rinsing the filter cake. The rinsing step can be performed at a temperature between about 0° C. and about 60° C. (e.g., about 40-60° C., about 45-55° C., or at about room temperature) with an organic solvent (e.g., an alcohol such as ethanol) to obtain a rinsed filter cake.

In one embodiment, the process further comprises, after rinsing the filter cake, drying the rinsed filter cake. The drying step can be performed at a temperature between about 0° C. and about 60° C. (e.g., about 40-60° C., about 45-55° C., or at about room temperature) to obtain Form I of Compound A.

In one embodiment, Form I has a purity of greater than 91%, e.g., greater than 92.5%, greater than 95%, greater than 96%, greater than 97%, or greater than 97.5%.

In one embodiment, Form I has a purity of greater than 98%, e.g., greater than 98.5%, greater than 99%, greater than 99.2%, greater than 99.5%, or greater than 99.8%.

In another aspect, the disclosure provides compounds such as

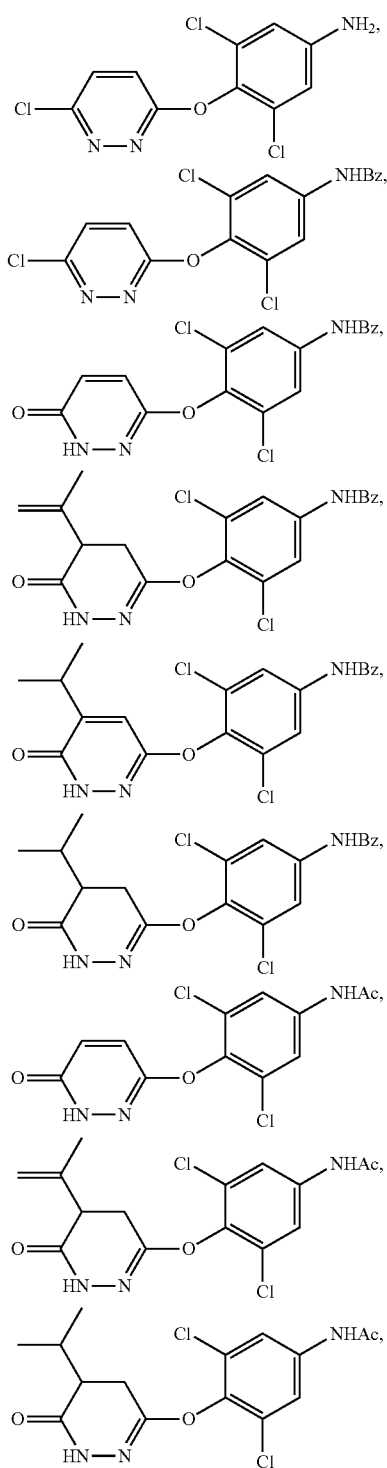

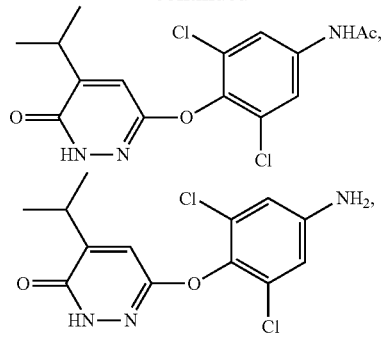

and a salt thereof, e.g., useful in synthesizing 6-(4-amino-2, 6-dichlorophenoxy)-4-isopropylpyridazin-3(2H)-one ("Int. 7").

The disclosure also provides a method for treating a resistance to thyroid hormone (RTH) in a subject in need thereof. The method comprises administering to a subject having at least one TRβ mutation a therapeutically effective amount of a compound of Formula (IV):

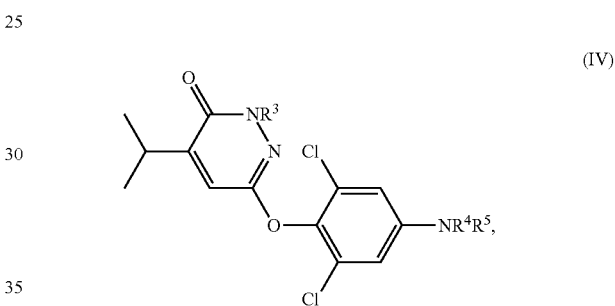

(IV)

wherein $R^3$ is H or $CH_2R_a$, in which $R_a$ is hydroxyl, O-linked amino acid, —OP(O)(OH)$_2$ or —OC(O)—$R_b$, $R_b$ being lower alkyl, alkoxy, alkyl acid, cycloalkyl, aryl, heteroaryl, or —(CH$_2$)$_n$-heteroaryl and n being 0 or 1;

$R^4$ is H, and $R^5$ is CH$_2$COOH, C(O)CO$_2$H, or an ester or amide thereof, or $R^4$ and $R^5$ together are —N=C(R$_c$)—C(O)—NH—C(O)—; in which R$_c$ is H or cyano.

Resistance to thyroid hormone (RTH) is a syndrome characterized by a variable tissue hyposensitivity to thyroid hormone and is primarily caused by autosomal dominant mutations to THRβ. See Shi et al., *Biochemistry* 2005, 44, 4612-4626.

In one embodiment, the compound used in the above method is 2-(3,5-dichloro-4-((5-isopropyl-6-oxo-1,6-dihydropyridazin-3-yl)oxy)phenyl)-3,5-dioxo-2,3,4,5-tetrahydro-1,2,4-triazine-6-carbonitrile ("Compound A"), e.g., Compound A in Form I.

In one embodiment, the subject to be treated by the above method has obesity, hyperlipidemia, hypercholesterolemia, diabetes, non-alcoholic steatohepatitis, fatty liver, bone disease, thyroid axis alteration, atherosclerosis, a cardiovascular disorder, tachycardia, hyperkinetic behavior, hypothyroidism, goiter, attention deficit hyperactivity disorder, learning disabilities, mental retardation, hearing loss, delayed bone age, neurologic or psychiatric disease or thyroid cancer.

In one embodiment, the THRβ mutation is selected from the group consisting of a substitution of threonine (T) for the wild type residue alanine (A) at amino acid position 234 of SEQ ID NO: 1 (A234T); a substitution of glutamine (Q) for the wild type residue arginine (R) at amino acid position 243 of SEQ ID NO: 1 (R243Q); a substitution of histidine (H) for the wild type residue arginine (R) at amino acid position 316 of SEQ ID NO: 1 (R316H); and a substitution of threonine (T) for the wild type residue alanine (A) at amino acid position 317 of SEQ ID NO: 1 (A317T). In another embodiment, the compound used in the method restores activity of mutant THRβ.

In one embodiment, the purity of compound of Formula (IV), such as Compound A, is obtained from reslurrying a crude compound from a suitable solvent described herein. In another embodiment, the compound is not a solvate (e.g., a hydrate).

In one embodiment, the compound of Formula (IV), e.g., Compound A, has a purity of greater than 85%, e.g., greater than 86%, greater than 90%, greater than 92.5%, greater than 95%, greater than 96%, greater than 97%, greater than 97.5%, greater than 98%, greater than 98.5%, greater than 99%, greater than 99.2%, greater than 99.5%, or greater than 99.8%.

In one embodiment, the compound of Formula (IV) is Compound A in Form I, and has a purity of greater than 85%, e.g., greater than 86%, greater than 90%, greater than 92.5%, greater than 95%, greater than 96%, greater than 97%, greater than 97.5%, greater than 98%, greater than 98.5%, greater than 99%, greater than 99.2%, greater than 99.5%, or greater than 99.8%.

In one embodiment, the compound of Formula (IV) is Compound A in Form I, and Form I has a purity of greater than 85%, e.g., greater than 86%, greater than 90%, greater than 92.5%, greater than 95%, greater than 96%, greater than 97%, greater than 97.5%, greater than 98%, greater than 98.5%, greater than 99%, greater than 99.2%, greater than 99.5%, or greater than 99.8%.

In one embodiment, the compound of Formula (IV), such as Compound A, has less than 1.5% (e.g., less than 1.0%, e.g., less than 0.5%) of the corresponding β-isopropylpyridazin-3 (2H)-one regioisomer (e.g., 2-(3,5-dichloro-4-((4-isopropyl-6-oxo-1,6-dihydropyridazin-3-yl)oxy)phenyl)-3,5-dioxo-2,3,4,5-tetrahydro-1,2,4-triazine-6-carbonitrile, the β-isopropylpyridazin-3(2H)-one regioisomer of Compound A).

In one embodiment, the compound of Formula (IV), such as Compound A, is free of the corresponding β-isopropylpyridazin-3(2H)-one regioisomer (e.g., 2-(3,5-dichloro-4-((4-isopropyl-6-oxo-1,6-dihydropyridazin-3-yl)oxy)phenyl)-3,5-dioxo-2,3,4,5-tetrahydro-1,2,4-triazine-6-carbonitrile, the β-isopropylpyridazin-3(2H)-one regioisomer of Compound A).

In one embodiment, the compound of Formula (IV), such as Compound A, has less than 1.5% (e.g., less than 1.0%, e.g., less than 0.5%) of heavy metal, e.g., silver, gold, or platinum.

In one embodiment, the subject is a mammal. In another embodiment, the subject is a human.

The disclosure further provides a method for determining a responsiveness of a subject to the compound of Formula (IV) or a pharmaceutically acceptable salt thereof, the method comprising:
 (a) providing a sample from the subject; and
 (b) detecting a mutation in a thyroid hormone receptor ("TR"), wherein the presence of the mutation indicates the subject is responsive to the compounds or a pharmaceutically acceptable salt thereof.

In one embodiment, the compound of Formula (IV) is 2-(3,5-dichloro-4-((5-isopropyl-6-oxo-1,6-dihydropyridazin-3-yl)oxy)phenyl)-3,5-dioxo-2,3,4,5-tetrahydro-1,2,4-triazine-6-carbonitrile ("Compound A").

In one embodiment, the TR is TRβ.

In one embodiment, the subject treated by the method of this invention has obesity, hyperlipidemia, hypercholesterolemia, diabetes, non-alcoholic steatohepatitis, fatty liver, bone disease, thyroid axis alteration, atherosclerosis, a cardiovascular disorder, tachycardia, hyperkinetic behavior, hypothyroidism, goiter, attention deficit hyperactivity disorder, learning disabilities, mental retardation, hearing loss, delayed bone age, neurologic or psychiatric disease or thyroid cancer.

In one embodiment, a method for determining a responsiveness to the compound of Formula (IV) can be used together with the method for treating a resistance to thyroid hormone. That is, before the treatment, a subject is tested to determine the responsiveness to the compound.

Other features and advantages of the present invention are apparent from detailed description, examples, and claims.

DETAILED DESCRIPTION OF THE INVENTION

Figure 1:
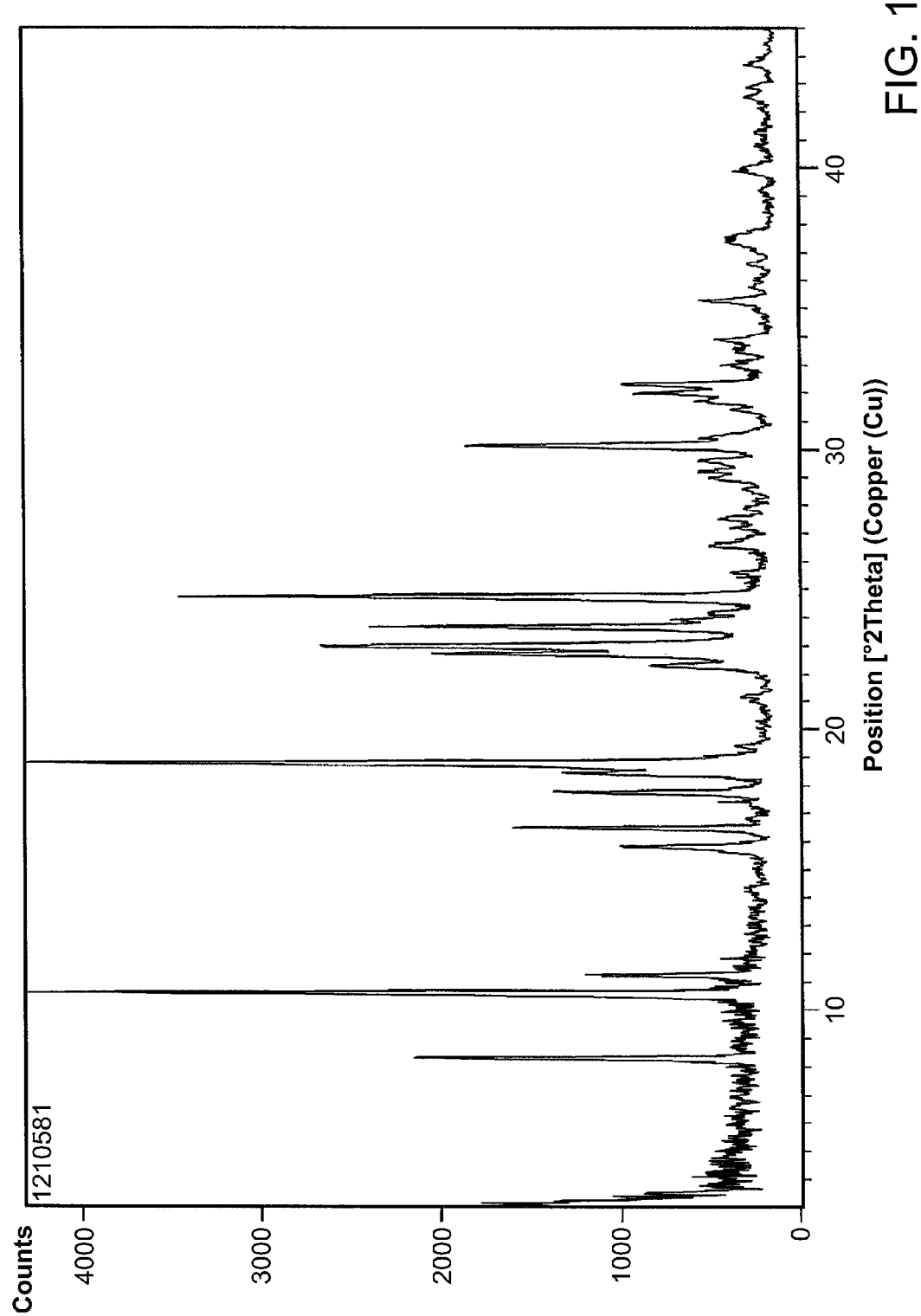
FIG. 1 is an X-ray powder diffractogram (XRPD) of 2-(3,5-dichloro-4-((5-isopropyl-6-oxo-1,6-dihydropyridazin-3-yl)oxy)phenyl)-3,5-dioxo-2,3,4,5-tetrahydro-1,2,4-triazine-6-carbonitrile ("Compound A") Form I.

As used in the specification and the appended claims, the singular forms "a," "an," and "the" include plural referents unless the context clearly dictates otherwise. Thus, for example, reference to "a reactant" includes not only a single reactant but also a combination or mixture of two or more different reactant, reference to "a substituent" includes a single substituent as well as two or more substituents, and the like.

As used herein, the phrases "for example," "for instance," "such as," or "including" are meant to introduce examples that further clarify more general subject matter. These examples are provided only as an aid for understanding the disclosure, and are not meant to be limiting in any fashion. Furthermore as used herein, the terms "may," "optional," "optionally," or "may optionally" mean that the subsequently described circumstance may or may not occur, so that the description includes instances where the circumstance occurs and instances where it does not. For example, the phrase "optionally present" means that an object may or may not be present, and, thus, the description includes instances wherein the object is present and instances wherein the object is not present.

In describing and claiming the present invention, the following terminology will be used in accordance with the definitions set out below.

As used herein, the abbreviation "TR" or "THR" refers to thyroid hormone receptor. TR nucleic acids and polypeptides from various species (e.g., human, rat, chicken, etc.) have previously been described. See, e.g., R. L. Wagner et al. (2001), *Molecular Endocrinology* 15(3): 398-410; J. Sap et al. (1986), *Nature* 324:635-640; C. Weinberger et al. (1986), *Nature* 324:641-646; and C. C. Tompson et al. (1986), *Science* 237:1610-1614; each of which is incorporated herein by reference in its entirety. The amino acid sequence of human TRβ is provided, e.g., by Genbank Accession No. P10828.2, incorporated herein by reference.

```
Amino acid sequence of the ligand binding
domain (residues 203-461) of human TRβ
                                       (SEQ ID NO: 1)
ELQKSIGHKPEPTDEEWELIKTVTEAHVATNAQGSHWKQKRKFLPEDIGQ

APIVNAPEGGKVDLEAFSHFTKIITPAITRVVDFAKKLPMFCELPCEDQI

ILLKGCCMEIMSLRAAVRYDPESETLTLNGEMAVTRGQLKNGGLGVVSDA

IFDLGMSLSSFNLDDTEVALLQAVLLMSSDRPGLACVERIEKYQDSFLLA

FEHYINYRKHHVTHFWPKLLMKVTDLRMIGACHASRFLHMKVECPTELFP

PLFLEVFED
```

The residues at the 234, 243, 316, and 317 positions of human TRβ are underlined in SEQ ID NO: 1. The portion of the human TRβ nucleotide sequence that encodes the above amino acid sequence is SEQ ID NO: 2. The nucleotide sequence of human TRβ is provided, e.g., by Genbank Accession No. NM_000461.4, incorporated herein by reference.

```
Nucleic acid sequence encoding the ligand
binding domain of human TRβ
                                       (SEQ ID NO: 2)
GAGCTGCAGAAGTCCATCGGGCACAAGCCAGAGCCCACAGACGAGGAATG

GGAGCTCATCAAAACTGTCACCGAAGCCCATGTGGCGACCAACGCCCAAG

GCAGCCACTGGAAGCAAAAACGGAAATTCCTGCCAGAAGACATTGGACAA

GCACCAATAGTCAATGCCCCAGAAGGTGGAAAGGTTGACTTGGAAGCCTT

CAGCCATTTTACAAAAATCATCACACCAGCAATTACCAGAGTGGTGGATT

TTGCCAAAAAGTTGCCTATGTTTTGTGAGCTGCCATGTGAAGACCAGATC

ATCCTCCTCAAAGGCTGCTGCATGGAGATCATGTCCCTTCGCGCTGCTGT
```

-continued
```
GCGCTATGACCCAGAAAGTGAGACTTTAACCTTGAATGGGGAAATGGCAG

TGACACGGGGCCAGCTGAAAAATGGGGGTCTTGGGGTGGTGTCAGACGCC

ATCTTTGACCTGGGCATGTCTCTGTCTTCTTTCAACCTGGATGACACTGA

AGTAGCCCTCCTTCAGGCCGTCCTGCTGATGTCTTCAGATCGCCCGGGGC

TTGCCTGTGTTGAGAGAATAGAAAAGTACCAAGATAGTTTCCTGCTGGCC

TTTGAACACTATATCAATTACCGAAAACACCACGTGACACACTTTTGGCC

AAAACTCCTGATGAAGGTGACAGATCTGCGGATGATAGGAGCCTGCCATG

CCAGCCGCTTCCTGCACATGAAGGTGGAATGCCCCACAGAACTCTTCCCC

CCTTTGTTCTTGGAAGTGTTCGAGGATTAG
```

As used herein, the phrase "having the formula" or "having the structure" is not intended to be limiting and is used in the same way that the term "comprising" is commonly used. The term "independently selected from" is used herein to indicate that the recited elements, e.g., R groups or the like, can be identical or different.

The term "alkyl" as used herein refers to a branched or unbranched saturated hydrocarbon group typically although not necessarily containing 1 to about 24 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl and the like. Generally, although not necessarily, alkyl groups herein may contain 1 to about 18 carbon atoms, and such groups may contain 1 to about 12 carbon atoms. The term "lower alkyl" intends an alkyl group of 1 to 6 carbon atoms, for example, 1, 2, 3, 4, 5, or 6 carbon atoms. "Substituted alkyl" refers to alkyl substituted with one or more substituent groups, and the terms "heteroatom-containing alkyl" and "heteroalkyl" refer to an alkyl substituent in which at least one carbon atom is replaced with a heteroatom, as described in further detail infra.

The term "alkenyl" as used herein refers to a linear, branched or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, and the like. Generally, although again not necessarily, alkenyl groups herein may contain 2 to about 18 carbon atoms, and for example may contain 2 to 12 carbon atoms. The term "lower alkenyl" intends an alkenyl group of 2 to 6 carbon atoms. The term "substituted alkenyl" refers to alkenyl substituted with one or more substituent groups, and the terms "heteroatom-containing alkenyl" and "heteroalkenyl" refer to alkenyl in which at least one carbon atom is replaced with a heteroatom, e.g., N, P, O, or S.

The term "alkynyl" as used herein refers to a linear or branched hydrocarbon group of 2 to 24 carbon atoms containing at least one triple bond, such as ethynyl, n-propynyl, and the like. Generally, although again not necessarily, alkynyl groups herein may contain 2 to about 18 carbon atoms, and such groups may further contain 2 to 12 carbon atoms. The term "lower alkynyl" intends an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom.

The term "alkoxy" as used herein intends an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms, and includes, for example, methoxy, ethoxy, n-propoxy, isopropoxy, t-butyloxy, etc. Substituents identified as "$C_1$-$C_6$ alkoxy" or "lower alkoxy" herein may, for example, may contain 1 to 3 carbon atoms, and as a further example, such substituents may contain 1 or 2 carbon atoms (i.e., methoxy and ethoxy).

The term "alkyl acid" refers to an acid substituent that is on an alkyl group, such as —$(CH_2)_o$COOH, in which o is an integer between 1 and 6. The alkyl group can either be linear or branched.

The term "aryl" as used herein, and unless otherwise specified, refers to an aromatic substituent generally, although not necessarily, containing 5 to 30 carbon atoms and containing a single aromatic ring or multiple aromatic rings that are fused together, directly linked, or indirectly linked (such that the different aromatic rings are bound to a common group such as a methylene or ethylene moiety). Aryl groups may, for example, contain 5 to 20 carbon atoms, and as a further example, aryl groups may contain 5 to 12 carbon atoms. For example, aryl groups may contain one aromatic ring or two fused or linked aromatic rings, e.g., phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl substituent, in which at least one carbon atom is replaced with a heteroatom, as will be described in further detail infra. If not otherwise indicated, the term "aryl" includes rings that are unsubstituted, substituted, and/or have heteroatom-containing aromatic substituents.

The term "aralkyl" refers to an alkyl group with an aryl substituent, and the term "alkaryl" refers to an aryl group with an alkyl substituent, wherein "alkyl" and "aryl" are as defined above. In general, aralkyl and alkaryl groups herein contain 6 to 30 carbon atoms. Aralkyl and alkaryl groups may, for example, contain 6 to 20 carbon atoms, and as a further example, such groups may contain 6 to 12 carbon atoms.

The term "amino" is used herein to refer to the group —$NZ^1Z^2$ wherein $Z^1$ and $Z^2$ are hydrogen or nonhydrogen substituents, with nonhydrogen substituents including, for example, alkyl, aryl, alkenyl, aralkyl, and substituted and/or heteroatom-containing variants thereof.

The terms "halo" and "halogen" are used in the conventional sense to refer to a chloro, bromo, fluoro or iodo substituent.

The term "heteroatom-containing" as in a "heteroatom-containing alkyl group" (also termed a "heteroalkyl" group) or a "heteroatom-containing aryl group" (also termed a "heteroaryl" group) refers to a molecule, linkage or substituent in which one or more carbon atoms are replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the term "heterocycle" or "heterocyclic" refers to a cyclic moiety that is heteroatom-containing, the terms "heteroaryl" and "heteroaromatic" respectively refer to "aryl" and "aromatic" substituents that are heteroatom-containing, and the like. Examples of heteroalkyl groups include alkoxyaryl, alkylsulfanyl-substituted alkyl, N-alkylated amino alkyl, and the like. Examples of heteroaryl substituents include pyrrolyl, pyrrolidinyl, pyridinyl, quinolinyl, indolyl, furyl, pyrimidinyl, imidazolyl, 1,2,4-triazolyl, tetrazolyl, etc., and examples of heteroatom-containing alicyclic groups are pyrrolidino, morpholino, piperazino, piperidino, tetrahydrofuranyl, etc.

"Hydrocarbyl" refers to univalent hydrocarbyl radicals containing 1 to about 30 carbon atoms, including 1 to about 24 carbon atoms, further including 1 to about 18 carbon atoms, and further including about 1 to 12 carbon atoms, including linear, branched, cyclic, saturated and unsaturated species, such as alkyl groups, alkenyl groups, aryl groups, and the like. "Substituted hydrocarbyl" refers to hydrocarbyl substituted with one or more substituent groups, and the term "heteroatom-containing hydrocarbyl" refers to hydrocarbyl in which at least one carbon atom is replaced with a heteroatom.

The term "O-linked amino acid" means any amino acid, naturally occurring or synthetic, linked to a molecule via an oxygen of a carboxyl group of the amino acid, preferably via the carboxyl group of the carboxy terminus of the amino acid.

As used herein, the term "protecting group" means that a particular functional moiety, e.g., O, S, or N, is temporarily blocked so that a reaction can be carried out selectively at another reactive site in a multifunctional compound. In preferred embodiments, a protecting group reacts selectively in good yield to give a protected substrate that is stable to the projected reactions; the protecting group must be selectively removed in good yield by readily available, preferably nontoxic reagents that do not attack the other functional groups; the protecting group forms an easily separable derivative (more preferably without the generation of new stereogenic centers); and the protecting group has a minimum of additional functionality to avoid further sites of reaction. As detailed herein, oxygen, sulfur, nitrogen and carbon protecting groups may be utilized. For example, in certain embodiments, certain exemplary oxygen protecting groups may be utilized. These oxygen protecting groups include, but are not limited to methyl ethers, substituted methyl ethers (e.g., MOM (methoxymethyl ether), MTM (methylthiomethyl ether), BOM (benzyloxymethyl ether), and PMBM (p-methoxybenzyloxymethyl ether)), substituted ethyl ethers, substituted benzyl ethers, silyl ethers (e.g., TMS (trimethylsilyl ether), TES (triethylsilylether), TIPS (triisopropylsilyl ether), TBDMS (t-butyldimethylsilyl ether), tribenzyl silyl ether, and TBDPS (t-butyldiphenyl silyl ether), esters (e.g., formate, acetate, benzoate (Bz), trifluoroacetate, and dichloroacetate), carbonates, cyclic acetals and ketals. In certain other exemplary embodiments, nitrogen protecting groups are utilized. Nitrogen protecting groups, as well as protection and deprotection methods are known in the art. Nitrogen protecting groups include, but are not limited to, carbamates (including methyl, ethyl and substituted ethyl carbamates (e.g., Troc), amides, cyclic imide derivatives, N-Alkyl and N-Aryl amines, imine derivatives, and enamine derivatives. In yet other embodiments, certain exemplary sulfur protecting groups may be utilized. The sulfur protecting groups include, but are not limited to those oxygen protecting group describe above as well as aliphatic carboxylic acid (e.g., acrylic acid), maleimide, vinyl sulfonyl, and optionally substituted maleic acid. Certain other exemplary protecting groups are detailed herein, however, it will be appreciated that the present invention is not intended to be limited to these protecting groups; rather, a variety of additional equivalent protecting groups can be readily identified using the above criteria and utilized in the present invention. Additionally, a variety of protecting groups are described in "Protective Groups in Organic Synthesis" Third Ed. Greene, T. W. and Wuts, P. G., Eds., John Wiley & Sons, New York: 1999, the entire contents of which are hereby incorporated by reference.

By "substituted" as in "substituted hydrocarbyl," "substituted alkyl," "substituted aryl," and the like, as alluded to in some of the aforementioned definitions, is meant that in the hydrocarbyl, alkyl, aryl, or other moiety, at least one hydrogen atom bound to a carbon (or other) atom is replaced with one or more non-hydrogen substituents. Examples of such substituents include, without limitation, functional groups and the hydrocarbyl moieties $C_1$-$C_{24}$ alkyl (including $C_1$-$C_{18}$ alkyl, further including $C_1$-$C_{12}$ alkyl, and further including $C_1$-$C_6$ alkyl), $C_2$-$C_{24}$ alkenyl (including $C_2$-$C_{18}$ alkenyl, further including $C_2$-$C_{12}$ alkenyl, and further including $C_2$-$C_6$ alkenyl), $C_2$-$C_{24}$ alkynyl (including $C_2$-$C_{18}$ alkynyl, further including $C_2$-$C_{12}$ alkynyl, and further including $C_2$-$C_6$ alkynyl), $C_5$-$C_{30}$ aryl (including $C_5$-$C_{20}$ aryl, and further including $C_5$-$C_{12}$ aryl), and $C_6$-$C_{30}$ aralkyl (including $C_6$-$C_{20}$ aralkyl, and further including $C_6$-$C_{12}$ aralkyl).

By "functional group," as alluded to in some of the aforementioned definitions, is meant a non-hydrogen group comprising one or more non-hydrocarbon functionality. Examples of functional groups include, without limitation: halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), halocarbonyl (—CO)—X where X is halo), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO⁻), carbamoyl (—(CO)—NH$_2$), mono-substituted $C_1$-$C_{24}$ alkylcarbamoyl (—(CO)—NH($C_1$-$C_{24}$ alkyl)), di-substituted alkylcarbamoyl (—(CO)—N($C_1$-$C_{24}$ alkyl)$_2$), mono-substituted arylcarbamoyl (—(CO)—NH-aryl), thiocarbamoyl (—(CS)—NH$_2$), carbamido (—NH—(CO)—NH$_2$), cyano (—C≡N), isocyano (—N⁺≡C⁻), cyanato (—O—C≡N), isocyanato (—O—N⁺≡C⁻), isothiocyanato (—S—C≡N), azido (—N=N⁺=N⁻), formyl (—(CO)—H), thioformyl (—(CS)—H), amino (—NH$_2$), mono- and di-($C_1$-$C_{24}$ alkyl)-substituted amino, mono- and di-($C_5$-$C_{20}$ aryl)-substituted amino, $C_2$-$C_{24}$ alkylamido (—NH—(CO)-alkyl), $C_5$-$C_{20}$ arylamido (—NH—(CO)-aryl), imino (—CR=NH where R=hydrogen, $C_1$-$C_{24}$ alkyl, $C_5$-$C_{20}$ aryl, $C_6$-$C_{20}$ alkaryl, $C_6$-$C_{20}$ aralkyl, etc.), alkylimino (—CR=N(alkyl), where R=hydrogen, alkyl, aryl, alkaryl, etc.), arylimino (—CR=N(aryl), where R=hydrogen, alkyl, aryl, alkaryl, etc.), nitro (—NO$_2$), nitroso (—NO), sulfo (—SO$_2$—OH), sulfonato (—SO$_2$—O⁻), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), phosphono (—P(O)(OH)$_2$), phosphonato (—P(O)(O⁻)$_2$), phosphinato (—P(O)(O⁻)), phospho (—PO$_2$), and phosphino (—PH$_2$), mono- and di-($C_1$-$C_{24}$ alkyl)-substituted phosphino, mono- and di-($C_5$-$C_{20}$ aryl)-substituted phosphino; and the hydrocarbyl moieties $C_1$-$C_{24}$ alkyl (including $C_1$-$C_{18}$ alkyl, further including $C_1$-$C_{12}$ alkyl, and further including $C_1$-$C_6$ alkyl), $C_2$-$C_{24}$ alkenyl (including $C_2$-$C_{18}$ alkenyl, further including $C_2$-$C_{12}$ alkenyl, and further including $C_2$-$C_6$ alkenyl), $C_2$-$C_{24}$ alkynyl (including $C_2$-$C_{18}$ alkynyl, further including $C_2$-$C_{12}$ alkynyl, and further including $C_2$-$C_6$ alkynyl), $C_5$-$C_{30}$ aryl (including $C_5$-$C_{20}$ aryl, and further including $C_5$-$C_{12}$ aryl), and $C_6$-$C_{30}$ aralkyl (including $C_6$-$C_{20}$ aralkyl, and further including $C_6$-$C_{12}$ aralkyl). In addition, the aforementioned functional groups may, if a particular group permits, be further substituted with one or more additional functional groups or with one or more hydrocarbyl moieties such as those specifically enumerated above. Analogously, the above-mentioned hydrocarbyl moieties may be further substituted with one or more functional groups or additional hydrocarbyl moieties such as those specifically enumerated.

The term "telescoping a process" refers to collapsing a multistep process into a smaller number of steps or unit operations. A unit operation includes transformations, but also encompasses handling and isolation steps. Centrifugation, filtration, distillation, decantation, precipitation/crystallization, and packaging are examples of unit operations. There are a great many examples of telescoping and other process improvements in the literature (see, e.g., *J. Org. Chem.*, 2007, 72, 9757-9760).

It will be appreciated that some of the abovementioned definitions may overlap, such that some chemical moieties may fall within more than one definition.

When the term "substituted" appears prior to a list of possible substituted groups, it is intended that the term apply to every member of that group. For example, the phrase "substituted alkyl and aryl" is to be interpreted as "substituted alkyl and substituted aryl."

The disclosure provides methods of synthesizing a compound, e.g., one that is useful as an intermediate for synthesizing the pyridazinone compounds as thyroid hormone analogs. Pyridazinone compounds as thyroid hormone analogs, as well as their prodrugs, have been disclosed in e.g., U.S. Pat. Nos. 7,452,882, 7,807,674, and 8,076,334.

In particular, the invention features a method of making 6-(4-amino-2,6-dichlorophenoxy)-4-isopropylpyridazin-3 (2H)-one ("Int. 7") or a salt thereof, the method comprising:
(a) contacting $R^1MgX$ or $R^1Li$ with a compound of Formula (I):

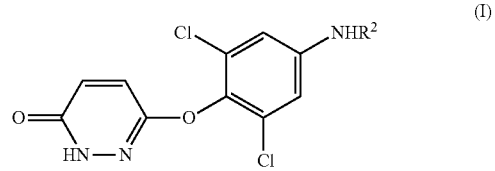

to form a compound of Formula (II):

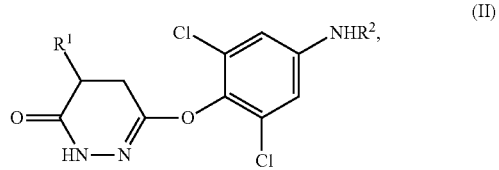

in which $R^1$ is isopropyl or isopropenyl, X is halo and $R^2$ is H or an amine protecting group; and
(b) converting the compound of Formula (II) to a compound of Formula (III):

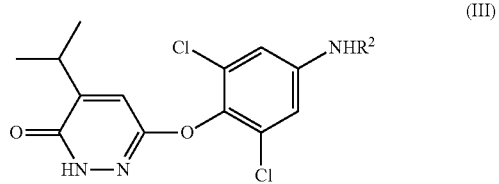

in the presence of a base when $R^1$ is isopropenyl or in the presence of an oxidizing agent when $R^1$ is isopropyl.

The present disclosure also describes a method for synthesizing the pyridazinone compounds as thyroid hormone analogs, as well as their prodrugs. Such compounds include those disclosed in U.S. Pat. Nos. 7,452,882, 7,807,674, and 8,076,334. In particular, the disclosure describes a method of making a compound of Formula (IV) or a pharmaceutically acceptable salt thereof:

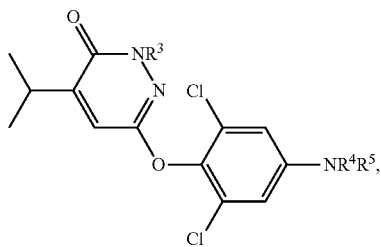

wherein
$R^3$ is H or $CH_2R_a$, in which $R_a$ is hydroxyl, O-linked amino acid, —OP(O)(OH)$_2$ or —OC(O)—$R_b$, $R_b$ being lower alkyl, alkoxy, alkyl acid, cycloalkyl, aryl, heteroaryl, or —(CH$_2$)$_n$-heteroaryl and n being 0 or 1;
$R^4$ is H, and $R^5$ is $CH_2COOH$, $C(O)CO_2H$, or an ester or amide thereof, or $R^4$ and $R^5$ together are —N═C($R_c$)—C(O)—NH—C(O)—; in which $R_c$ is H or cyano. The method comprises:
(a) contacting $R^1MgX$ or $R^1Li$ with a compound of Formula (I):

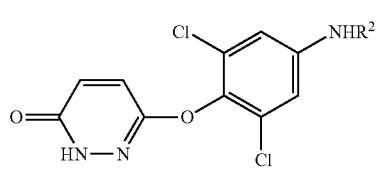

to form a compound of Formula (II):

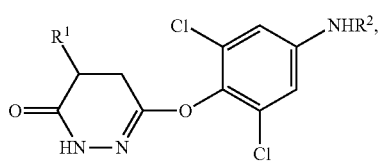

in which $R^1$ is isopropyl or isopropenyl, X is halo and $R^2$ is H or an amine protecting group; and
(b) converting the compound of Formula (II) to a compound of Formula (III):

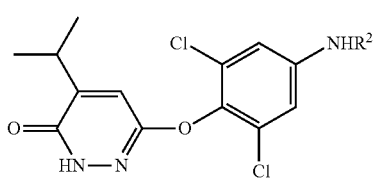

in the presence of a base when $R^1$ is isopropenyl or in the presence of bromine and an acid when $R^1$ is isopropyl,
(c) when present, removing the amine protecting group $R^2$ of the compound of Formula (III) to form 6-(4-amino-2,6-dichlorophenoxy)-4-isopropylpyridazin-3(2H)-one; and, optionally
(d) converting 6-(4-amino-2,6-dichlorophenoxy)-4-isopropylpyridazin-3(2H)-one to the compound of Formula (IV) under a suitable condition.

The present invention also provides detailed methods for the synthesis of various disclosed compounds of the present invention according to the following schemes and as shown in the Examples.

Throughout the description, where compositions are described as having, including, or comprising specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the invention remains operable. Moreover, two or more steps or actions can be conducted simultaneously.

The synthetic processes of the invention can tolerate a wide variety of functional groups, therefore various substituted starting materials can be used. The processes generally provide the desired final compound at or near the end of the overall process, although it may be desirable in certain instances to further convert the compound to a pharmaceutically acceptable salt, ester or prodrug thereof.

In embodiments, 6-(4-amino-2,6-dichlorophenoxy)-4-isopropylpyridazin-3(2H)-one ("Int. 7") is prepared according to Scheme 1 or 2 below.

Scheme 1: Synthesis of 6-(4-amino-2,6-dichlorophenoxy)-4-isopropylpyridazin-3(2H)-one (Int. 7) with isopropyl Grignard reagent (iPrMgX)

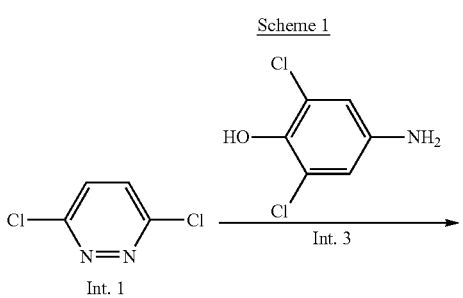

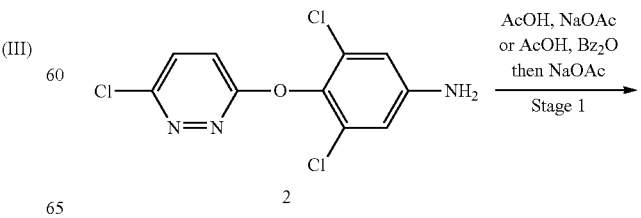

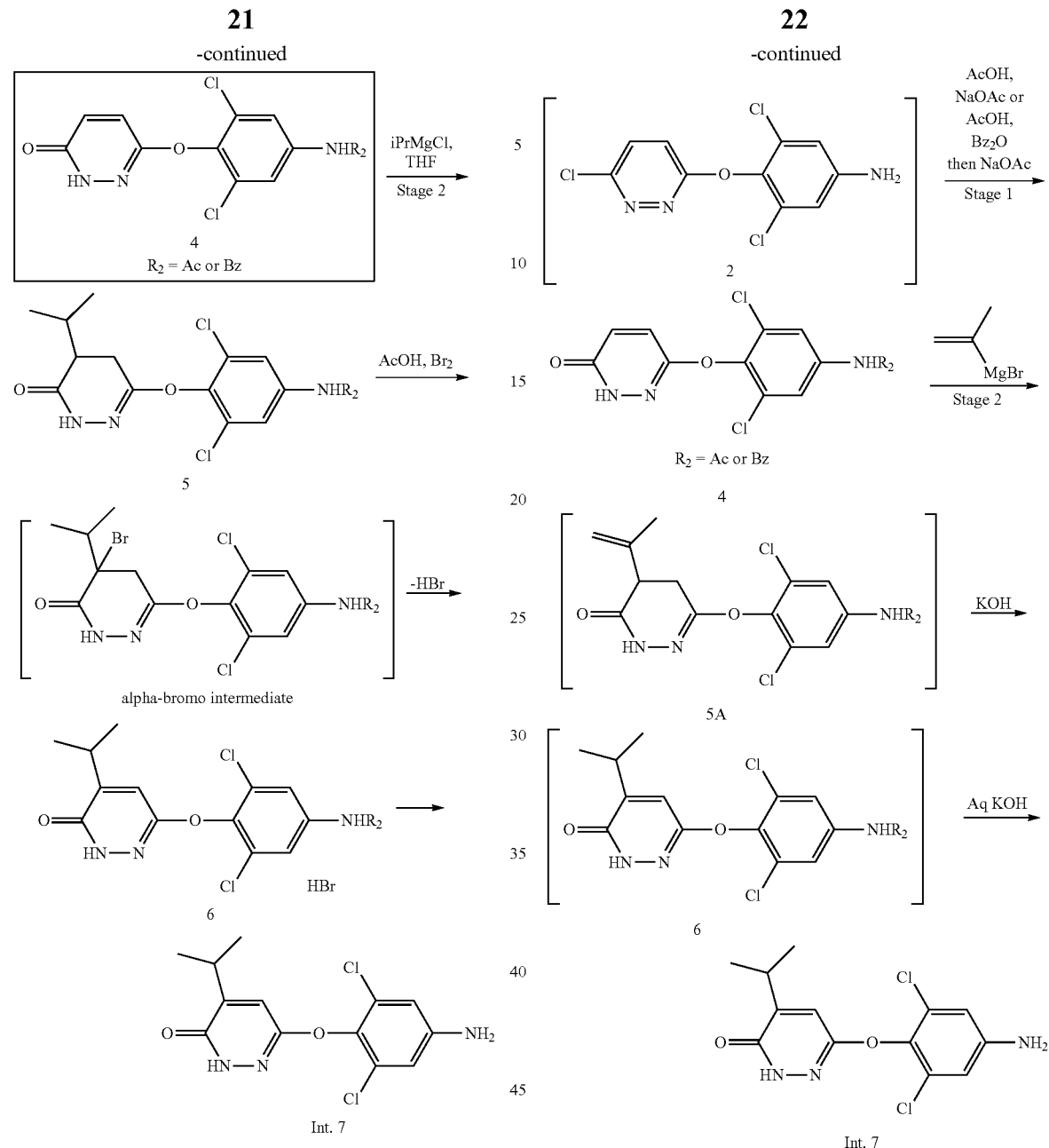

Scheme 2: Synthesis of 6-(4-amino-2,6-dichlorophenoxy)-4-isopropylpyridazin-3(2H)-one (Int. 7) with isopropenyl Grignard reagent Stage 1: Synthesis of 3,5-dichloro-4-((6-chloropyridazin-3-yl)oxy)aniline (Compound 2) and N-(3,5-dichloro-4-((6-oxo-1,6-dihydropyridazin-3-yl)oxy)phenyl)benzamide or N-(3,5-dichloro-4-((6-oxo-1,6-dihydropyridazin-3-yl)oxy)phenyl)acetamide (Compound 4)

Compound 2 is prepared by contacting 3,6-dichloropyridazine with 2,6-dichloro-4-aminophenol in the presence of a small amount of a suitable base such as a metal carbonate (e.g., cesium or potassium carbonate) or a metal alkoxide (e.g., potassium t-butoxide) in a suitable organic solvent (e.g., DMSO or DMAC) at a suitable reaction temperature (e.g., 60 to 120° C.) until completion of reaction, typically about 3 to 30 hours, for example about 3 to 15 hours.

Compound 4 is prepared by protecting 2 with a suitable amine protecting reagent (such as benzoic anhydride or ben-

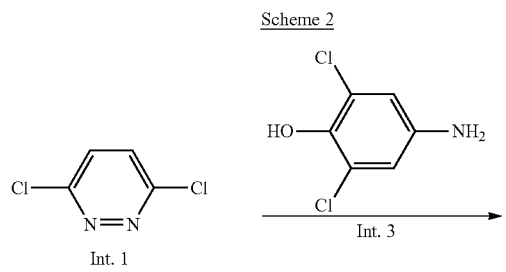

Scheme 2 zoic chloride) followed by treatment of the protected intermediate with sodium acetate in the presence of a suitable organic solvent (such as acetic acid) at a suitable reaction temperature (e.g., 100 to 120° C.) until completion of reaction, typically about 2 to 20 hours, for example about 5 to 15 hours. The crude product is purified with a suitable solvent (e.g., a mixture of water and acetic acid) at a suitable temperature (e.g., 88-100° C.). The acetate protected Compound 4 can be prepared by subjecting Compound 2 to the hydrolysis conditions.

Stage 2: Synthesis of N-(3,5-dichloro-4-((5-isopropyl-6-oxo-1,6-dihydropyridazin-3-yl)oxy)phenyl) benzamide or N-(3,5-dichloro-4-((5-isopropyl-6-oxo-1,6-dihydropyridazin-3-yl)oxy)phenyl) acetamide (Compound 6) and 6-(4-amino-2,6-dichlorophenoxy)-4-isopropylpyridazin-3(2H)-one (Int. 7)

Compound 6 is prepared by contacting Compound 4 with an isopropyl Grignard in a suitable organic solvent (such as tetrahydrofuran or dioxane) followed by an oxidation step. The oxidation step can be performed in the presence of an oxidizing reagent such as bromine in a suitable organic solvent such as acetic acid at a suitable reaction temperature (e.g., 60 to 90° C.) until completion of reaction, typically about 2 to 10 hours, for example about 2 to 5 hours.

It will be appreciated that a deprotection reaction is required in order to complete the transformation from Compound 6 to Int. 7. In particular, the N-protecting group (i.e., acetyl or benzoyl) must be removed in order to obtain the free amino present in Int. 7. Thus, in one embodiment, Int. 7 is obtained by deprotecting Compound 6 (where $R^2$ is Bz) with a base such as metal hydroxide (e.g., KOH or NaOH) or metal carbonate (e.g., sodium carbonate). In another embodiment, Int. 7 is obtained by deprotecting Compound 6 (where $R^2$ is Ac) with an acid such as trifluoroacetic acid.

Alternatively, Compound 7 is prepared by contacting Compound 4 with an isopropenyl Grignard in a suitable organic solvent (such as tetrahydrofuran or 2-methyl THF) followed by isomerization (e.g., from 5A to 6) and deprotection under the treatment of a base such as metal hydroxide (e.g., KOH). The isomerization/deprotection step is performed at a suitable reaction temperature (e.g., 60 to 90° C.) until completion of reaction, typically about 10 to 60 hours, for example about 16 hours at 90° C.

The Grignard reaction can be performed in the presence of a Lewis acid such as LiCl or LiBr at a suitable reaction temperature (e.g., room temperature to 40° C.) until completion of reaction, typically about 2 to 10 hours, for example about 2 to 5 hours.

In embodiments, the synthesis of compound 5 or 5A results in improved yield of Int. 7 relative to other methods known in the art. For example, the synthesis of 5 or 5A results in a yield of greater than 45%, 50%, 55%, 60%, 65%, 70%, 75%, 80%, 85% or greater than 90%.

In embodiments, the Grignard reaction improves regioselectivity, resulting in significantly less β-isopropyl regioisomer of compound 6, i.e.,

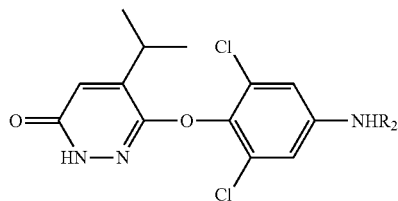

and thus more pure Int. 7.

In one embodiment, the conversion from 6-(4-amino-2,6-dichlorophenoxy)-4-isopropylpyridazin-3(2H)-one ("Int. 7") to Compound A is performed according to Scheme 3 below.

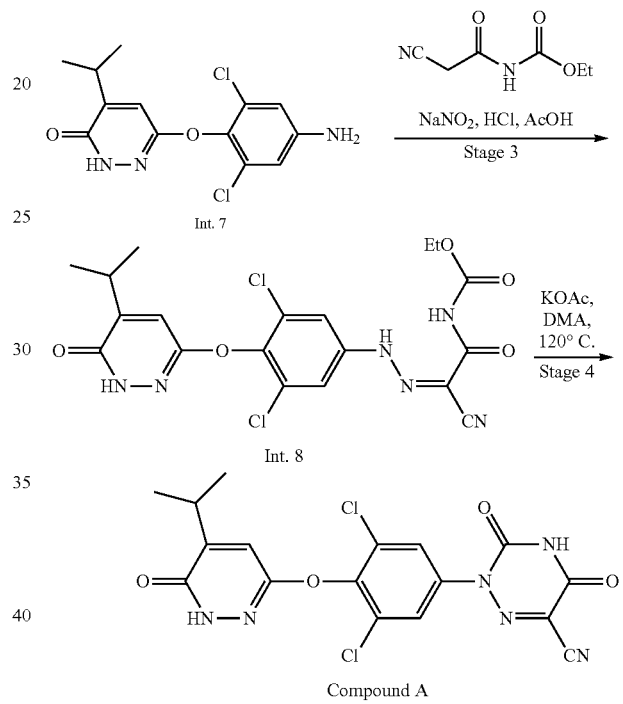

Compound A

Stage 3: Synthesis of 6-(4-amino-2,6-dichlorophenoxy)-4-isopropylpyridazin-3(2H)-one (Int. 8)

Int. 8 is prepared by contacting 6-(4-amino-2,6-dichlorophenoxy)-4-isopropylpyridazin-3(2H)-one with ethyl (2-cyanoacetyl)carbamate and a metal nitrite such as sodium nitrite in the presence of an acid (such as HCl) in a suitable solvent (e.g., a mixture of acetic acid and water) at a suitable reaction temperature (e.g., below 10° C.) until the reaction is complete.

Stage 4: Synthesis of 2-(3,5-dichloro-4-((5-isopropyl-6-oxo-1,6-dihydropyridazin-3-yl)oxy)phenyl)-3,5-dioxo-2,3,4,5-tetrahydro-1,2,4-triazine-6-carbonitrile (Compound A)

Compound A is prepared by contacting Int. 8 and a base such as sodium acetate or potassium acetate in a suitable solvent (e.g., DMAC) at a suitable reaction temperature (e.g., at about 120° C.) until the reaction is complete.

In embodiments, the conversion from 6-(4-amino-2,6-dichlorophenoxy)-4-isopropylpyridazin-3(2H)-one ("Int.

7'") to a compound of Formula (IV) other than MGL-3916 (such as prodrugs thereof) is performed under conditions described in, e.g., U.S. Pat. Nos. 7,452,882, 7,807,674, and 8,076,334, which are hereby incorporated by reference in their entireties.

The synthetic methods described herein result in superior regioselectivity, with the Grignard installation of the isopropenyl or isopropyl group versus the biaryl ether formation in the synthetic route previously disclosed in, e.g., U.S. Pat. No. 7,452,882, which gave poor regioselectivity. Further, by telescoping the biaryl ether formation into the benzamide protection, the methods disclosed herein avoid the isolation of the biaryl ether product, which was nearly practically impossible because of filtration times of greater than 1 week per batch when synthesizing this product in kilogram quantities.

The present invention provides, compounds with high purity and/or in specific morphic form (e.g., Form I), compositions described herein and methods for the treatment or prevention of obesity, hyperlipidemia, hypercholesterolemia, diabetes, non-alcoholic steatohepatitis, fatty liver, bone disease, thyroid axis alteration, atherosclerosis, a cardiovascular disorder, tachycardia, hyperkinetic behavior, hypothyroidism, goiter, attention deficit hyperactivity disorder, learning disabilities, mental retardation, hearing loss, delayed bone age, neurologic or psychiatric disease or thyroid cancer.

It will be appreciated that the methods disclosed herein are suitable for both large-scale and small-scale preparations of the desired compounds. In preferred embodiments of the methods described herein, the thyroid hormone analogs may be prepared on a large scale, for example on an industrial production scale rather than on an experimental/laboratory scale. For example, a batch-type process according to the methods of the disclosure allows the preparation of batches of at least 1 g, or at least 5 g, or at least 10 g, or at least 100 g, or at least 1 kg, or at least 100 kg of thyroid hormone analogs. Furthermore, the methods allow the preparation of a thyroid hormone analog having a purity of at least 98%, or at least 98.5% as measured by HPLC.

Pharmaceutical Compositions

The present invention also provides pharmaceutical compositions comprising a compound of Formula IV in combination with at least one pharmaceutically acceptable excipient or carrier.

A "pharmaceutical composition" is a formulation containing a compound of the present invention in a form suitable for administration to a subject. In one embodiment, the pharmaceutical composition is in bulk or in unit dosage form. The unit dosage form is any of a variety of forms, including, for example, a capsule, an IV bag, a tablet, a single pump on an aerosol inhaler or a vial. The quantity of active ingredient (e.g., a formulation of the disclosed compound or salt, hydrate, solvate or isomer thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this invention include powders, sprays, ointments, pastes, creams, lotions, gels, solutions, patches and inhalants. In one embodiment, the active compound is mixed under sterile conditions with a pharmaceutically acceptable carrier, and with any preservatives, buffers or propellants that are required.

As used herein, the phrase "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable excipient or carrier" means an excipient or carrier that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

The term "therapeutically effective amount", as used herein, refers to an amount of a pharmaceutical agent to treat, ameliorate, or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician. In a preferred aspect, the disease or condition to be treated is a metabolic disorder.

In the practice of the method of the present invention, an effective amount of any one of the compounds of this invention or a combination of any of the compounds of this invention or a pharmaceutically acceptable salt or ester thereof, is administered via any of the usual and acceptable methods known in the art, either singly or in combination. The compounds or compositions can thus be administered orally (e.g., buccal cavity), sublingually, parenterally (e.g., intramuscularly, intravenously, or subcutaneously), rectally (e.g., by suppositories or washings), transdermally (e.g., skin electroporation) or by inhalation (e.g., by aerosol), and in the form or solid, liquid or gaseous dosages, including tablets and suspensions. The administration can be conducted in a single unit dosage form with continuous therapy or in a single dose therapy ad libitum. The therapeutic composition can also be in the form of an oil emulsion or dispersion in conjunction with a lipophilic salt such as pamoic acid, or in the form of a biodegradable sustained-release composition for subcutaneous or intramuscular administration.

Useful pharmaceutical carriers for the preparation of the compositions hereof, can be solids, liquids or gases; thus, the compositions can take the form of tablets, pills, capsules, suppositories, powders, enterically coated or other protected formulations (e.g. binding on ion-exchange resins or packaging in lipid-protein vesicles), sustained release formulations, solutions, suspensions, elixirs, aerosols, and the like. The carrier can be selected from the various oils including those of petroleum, animal, vegetable or synthetic origin, e.g., peanut oil, soybean oil, mineral oil, sesame oil, and the like. Water, saline, aqueous dextrose, and glycols are preferred liquid carriers, particularly (when isotonic with the blood) for injectable solutions. For example, formulations for intravenous administration comprise sterile aqueous solutions of the active ingredient(s) which are prepared by dissolving solid active ingredient(s) in water to produce an aqueous solution, and rendering the solution sterile. Suitable pharmaceutical excipients include starch, cellulose, talc, glucose, lactose, talc, gelatin, malt, rice, flour, chalk, silica, magnesium stearate, sodium stearate, glycerol monostearate, sodium chloride, dried skim milk, glycerol, propylene glycol, water, ethanol, and the like. The compositions may be subjected to conventional pharmaceutical additives such as preservatives, stabilizing agents, wetting or emulsifying agents, salts for adjusting osmotic pressure, buffers and the like. Suitable pharmaceutical carriers and their formulation are described in Remington's Pharmaceutical Sciences by E. W. Martin. Such compositions will, in any event, contain an effective amount of the active compound together with a suitable carrier so as to prepare the proper dosage form for proper administration to the recipient.

The pharmaceutical preparations can also contain preserving agents, solubilizing agents, stabilizing agents, wetting agents, emulsifying agents, sweetening agents, coloring agents, flavoring agents, salts for varying the osmotic pressure, buffers, coating agents or antioxidants. They can also contain other therapeutically valuable substances, including additional active ingredients other than those of formula I.

The compounds of the present invention are useful as medicaments for the treatment of a resistance to thyroid hormone (RTH) in a subject who has at least one TRβ mutation. The subject may have a disease, such as obesity, hyperlipidemia, hypercholesterolemia, diabetes, non-alcoholic steatohepatitis, fatty liver, bone disease, thyroid axis alteration, atherosclerosis, a cardiovascular disorder, tachycardia, hyperkinetic behavior, hypothyroidism, goiter, attention deficit hyperactivity disorder, learning disabilities, mental retardation, hearing loss, delayed bone age, neurologic or psychiatric disease or thyroid cancer.

The therapeutically effective amount or dosage of a compound according to this invention can vary within wide limits and may be determined in a manner known in the art. For example, the drug can be dosed according to body weight. Such dosage will be adjusted to the individual requirements in each particular case including the specific compound(s) being administered, the route of administration, the condition being treated, as well as the patient being treated. In another embodiment, the drug can be administered by fixed does, e.g., dose not adjusted according to body weight. In general, in the case of oral or parenteral administration to adult humans, a daily dosage of from about 0.5 mg to about 1000 mg should be appropriate, although the upper limit may be exceeded when indicated. The dosage is preferably from about 5 mg to about 400 mg per day. A preferred dosage may be from about 20 mg to about 100 mg per day. The daily dosage can be administered as a single dose or in divided doses, or for parenteral administration it may be given as continuous infusion.

An effective amount of a pharmaceutical agent is that which provides an objectively identifiable improvement as noted by the clinician or other qualified observer. As used herein, the term "dosage effective manner" refers to amount of an active compound to produce the desired biological effect in a subject or cell.

The pharmaceutical compositions can be included in a container, pack, or dispenser together with instructions for administration.

The compounds of the present invention are capable of further forming salts. All of these forms are also contemplated within the scope of the claimed invention.

As used herein, "pharmaceutically acceptable salts" refer to derivatives of the compounds of the present invention wherein the parent compound is modified by making acid or base salts thereof. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, 1,2-ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, toluene sulfonic, and the commonly occurring amine acids, e.g., glycine, alanine, phenylalanine, arginine, etc.

Other examples of pharmaceutically acceptable salts include hexanoic acid, cyclopentane propionic acid, pyruvic acid, malonic acid, 3-(4-hydroxybenzoyl)benzoic acid, cinnamic acid, 4-chlorobenzenesulfonic acid, 2-naphthalenesulfonic acid, 4-toluenesulfonic acid, camphorsulfonic acid, 4-methylbicyclo-[2.2.2]-oct-2-ene-1-carboxylic acid, 3-phenylpropionic acid, trimethylacetic acid, tertiary butylacetic acid, muconic acid, and the like. The present invention also encompasses salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, diethylamine, diethylaminoethanol, ethylenediamine, imidazole, lysine, arginine, morpholine, 2-hydroxyethylmorpholine, dibenzylethylenediamine, trimethylamine, piperidine, pyrrolidine, benzylamine, tetramethylammonium hydroxide and the like.

It should be understood that all references to pharmaceutically acceptable salts include solvent addition forms (solvates) or crystal forms (polymorphs) as defined herein, of the same salt.

The compounds of the present invention can also be prepared as esters, for example, pharmaceutically acceptable esters. For example, a carboxylic acid function group in a compound can be converted to its corresponding ester, e.g., a methyl, ethyl or other ester. Also, an alcohol group in a compound can be converted to its corresponding ester, e.g., an acetate, propionate or other ester.

The compounds of the present invention can also be prepared as prodrugs, for example, pharmaceutically acceptable prodrugs. The terms "pro-drug" and "prodrug" are used interchangeably herein and refer to any compound which releases an active parent drug in vivo. Since prodrugs are known to enhance numerous desirable qualities of pharmaceuticals (e.g., solubility, bioavailability, manufacturing, etc.), the compounds of the present invention can be delivered in prodrug form. Thus, the present invention is intended to cover prodrugs of the presently claimed compounds, methods of delivering the same and compositions containing the same. "Prodrugs" are intended to include any covalently bonded carriers that release an active parent drug of the present invention in vivo when such prodrug is administered to a subject. Prodrugs in the present invention are prepared by modifying functional groups present in the compound in such a way that the modifications are cleaved, either in routine manipulation or in vivo, to the parent compound. Prodrugs include compounds of the present invention wherein a hydroxy, amino, sulfhydryl, carboxy or carbonyl group is bonded to any group that may be cleaved in vivo to form a free hydroxyl, free amino, free sulfhydryl, free carboxy or free carbonyl group, respectively.

Examples of prodrugs include, but are not limited to, esters (e.g., acetate, dialkylaminoacetates, formates, phosphates, sulfates and benzoate derivatives) and carbamates (e.g., N,N-dimethylaminocarbonyl) of hydroxy functional groups, esters (e.g., ethyl esters, morpholinoethanol esters) of carboxyl functional groups, N-acyl derivatives (e.g., N-acetyl) N-Mannich bases, Schiff bases and enaminones of amino functional groups, oximes, acetals, ketals and enol esters of ketone and aldehyde functional groups in compounds of the invention, and the like, See Bundegaard, H., *Design of Prodrugs*, p 1-92, Elesevier, New York-Oxford (1985).

The compounds, or pharmaceutically acceptable salts, esters or prodrugs thereof, are administered orally, nasally, transdermally, pulmonary, inhalationally, buccally, sublingually, intraperintoneally, subcutaneously, intramuscularly, intravenously, rectally, intrapleurally, intrathecally and parenterally. In one embodiment, the compound is administered orally. One skilled in the art will recognize the advantages of certain routes of administration.

The dosage regimen utilizing the compounds is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter or arrest the progress of the condition.

Techniques for formulation and administration of the disclosed compounds of the invention can be found in *Remington: the Science and Practice of Pharmacy*, 19$^{th}$ edition, Mack Publishing Co., Easton, Pa. (1995). In an embodiment, the compounds described herein, and the pharmaceutically acceptable salts thereof, are used in pharmaceutical preparations in combination with a pharmaceutically acceptable carrier or diluent. Suitable pharmaceutically acceptable carriers include inert solid fillers or diluents and sterile aqueous or organic solutions. The compounds will be present in such pharmaceutical compositions in amounts sufficient to provide the desired dosage amount in the range described herein.

The invention features a method for treating or alleviating a symptom of resistance to thyroid hormone in a subject by administering to a subject expressing a mutant TRβ comprising a mutation in the ligand-binding domain a therapeutically effective amount of a compound of Formula (IV), such as Compound A, e.g., Form I thereof.

The disclosure also provides a method of determining a responsiveness of a subject having resistance to thyroid hormone (RTH) to a compound of Formula (IV) disclosed herein by providing a sample from the subject; and detecting at least one TRβ mutation (e.g., a gene mutation or a mutation in the ligand-binding domain of TRβ polypeptide, e.g., a polypeptide as defined in SEQ ID NO: 1); and the presence of said mutation indicates the subject is responsive to a compound of Formula (IV), such as Compound A, e.g., Form I thereof. The method can further include treating the subject who has the mutation by administering with a therapeutically effective amount of a compound of Formula (IV), such as Compound A, e.g., Form I thereof.

In one embodiment, the subject that shows or will show responsiveness to a compound of Formula (IV) such as Compound A has obesity, hyperlipidemia, hypercholesterolemia, diabetes, non-alcoholic steatohepatitis, fatty liver, bone disease, thyroid axis alteration, atherosclerosis, a cardiovascular disorder, tachycardia, hyperkinetic behavior, hypothyroidism, goiter, attention deficit hyperactivity disorder, learning disabilities, mental retardation, hearing loss, delayed bone age, neurologic or psychiatric disease or thyroid cancer.

Further, the disclosure also provides a method which includes determining the presence of a TRβ gene mutation in a sample from a subject; and selecting, based on the presence of an TRβ gene mutation, a therapy that includes the administration of a therapeutically effective amount of a compound of Formula (IV), such as Compound A, e.g., Form I thereof.

The disclosure also provides a method which includes amplifying a nucleic acid in a sample from a subject with a primer that is complementary to a mutant TRβ nucleic acid sequence comprising a TRβ gene mutation in a nucleic acid sequence as defined in SEQ ID NO: 2; determining the presence of the amplified nucleic acid, and selecting, based on the presence of the amplified nucleic acid, a therapy that includes the administration of a therapeutically effective amount of a compound of Formula (IV), or treating the subject by administering a therapeutically effective amount of a compound of Formula (IV) based on the presence of the amplified nucleic acid.

The mutant TRβ described herein is a mutant TRβ polypeptide or a nucleic acid sequence encoding a mutant TRβ polypeptide.

In one embodiment, the mutant TRβ comprises one or more mutations at amino acid positions 234, 243, 316, and 317 of SEQ ID NO: 1. More preferably, mutation is selected from the group consisting of a substitution of threonine (T) for the wild type residue alanine (A) at amino acid position 234 of SEQ ID NO: 1 (A234T); a substitution of glutamine (Q) for the wild type residue arginine (R) at amino acid position 243 of SEQ ID NO: 1 (R243Q); a substitution of histidine (H) for the wild type residue arginine (R) at amino acid position 316 of SEQ ID NO: 1 (R316H); and a substitution of threonine (T) for the wild type residue alanine (A) at amino acid position 317 of SEQ ID NO: 1 (A317T).

In one embodiment, the mutant TRβ comprises a nucleic acid sequence encoding a mutant TRβ polypeptide having one or more mutations at amino acid positions 234, 243, 316, and 317 of SEQ ID NO: 1. A nucleic acid sequence encoding a mutant TRβ polypeptide or a peptide fragment that is characteristic of the mutant TRβ polypeptide can be detected using any suitable method. For example, a nucleic acid sequence encoding a mutant TRβ polypeptide can be detected using whole-genome resequencing or target region resequencing (the latter also known as targeted resequencing) using suitably selected sources of DNA and polymerase chain reaction (PCR) primers in accordance with methods well known in the art. See, for example, Bentley (2006) *Curr Opin Genet Dev*. 16:545-52, and Li et al. (2009) *Genome Res* 19:1124-32. The method typically and generally entails the steps of genomic DNA purification, PCR amplification to amplify the region of interest, cycle sequencing, sequencing reaction cleanup, capillary electrophoresis, and data analysis. High quality PCR primers to cover region of interest are designed using in silico primer design tools. Cycle sequencing is a simple method in which successive rounds of denaturation, annealing, and extension in a thermal cycler result in linear amplification of extension products. The products are typically terminated with a fluorescent tag that identifies the terminal nucleotide base as G, A, T, or C. Unincorporated dye terminators and salts that may compete for capillary eletrophoretic injection are removed by washing. During capillary electrophoresis, the products of the cycle sequencing reaction migrate through capillaries filled with polymer. The negatively charged DNA fragments are separated by size as they move through the capillaries toward the positive electrode. After electrophoresis, data collection software creates a sample file of the raw data. Using downstream software applications, further data analysis is performed to translate the collected color data images into the corresponding nucleotide bases. Alternatively or in addition, the method may include the use of microarray-based targeted region genomic DNA capture and/or sequencing. Kits, reagents, and methods for selecting appropriate PCR primers and performing resequencing are commercially available, for example, from Applied Biosystems, Agilent, and NimbleGen (Roche Diagnostics GmbH). For use in the instant invention, PCR primers may be selected so as to amplify, for example, at least a relevant portion of a nucleic acid sequence encoding a mutant TRβ polypeptide having one or more mutations at amino acid positions 234, 243, 316, and 317 of SEQ ID NO: 1.

Alternatively or in addition, a nucleic acid sequence encoding a mutant TRβ polypeptide may be detected using a Southern blot in accordance with methods well known in the art.

In certain embodiments, the methods of the invention comprise the step of performing an assay to detect a mutant of TRβ in a sample from a subject. As used herein, a "sample from a subject" refers to any suitable sample containing cells or components of cells obtained or derived from a subject. In one embodiment the sample is a blood sample. In one embodiment the sample is a biopsy sample obtained from, for example, the thyroid gland.

The disclosure also provides a ligand-mutant TRβ complex comprising: a mutant TRβ polypeptide and a compound of Formula (IV). For example, the mutant TRβ polypeptide forming the complex comprises one or more mutations at amino acid positions 234, 243, 316, and 317 of SEQ ID NO: 1. For example, the compound forming the complex is Compound A.

In addition, the disclosure provides a primer-nucleic acid complex comprising: a mutant TRβ nucleic acid sequence, and a PCR primer that is complementary to the mutant TRβ nucleic acid sequence, wherein the mutant nucleic acid sequence comprises an EZH2 gene mutation in a nucleic acid sequence as defined in SEQ ID NO: 2.

All patents, patent applications, and publications mentioned herein are hereby incorporated by reference in their entireties. However, where a patent, patent application, or publication containing express definitions is incorporated by reference, those express definitions should be understood to apply to the incorporated patent, patent application, or publication in which they are found, and not to the remainder of the text of this application, in particular the claims of this application.

It is to be understood that while the invention has been described in conjunction with the preferred specific embodiments thereof, that the foregoing description as well as the examples that follow, are intended to illustrate and not limit the scope of the invention. It will be understood by those skilled in the art that various changes may be made and equivalents may be substituted without departing from the scope of the invention, and further that other aspects, advantages and modifications will be apparent to those skilled in the art to which the invention pertains.

All percentages and ratios used herein, unless otherwise indicated, are by weight. Other features and advantages of the present invention are apparent from the different examples. The provided examples illustrate different components and methodology useful in practicing the present invention. The examples do not limit the claimed invention. Based on the present disclosure the skilled artisan can identify and employ other components and methodology useful for practicing the present invention.

EXAMPLES

Unless otherwise specified, the analytical instruments and parameters used for compounds described in the Examples are as follows:

The XRPD data were collected on X-Ray Powder Diffractometer (CubiX-Pro XRD) with Cu Kα radiation (45 kV, 40 mA) from 3 to 45 degrees 2-theta (2θ) at a scanning rate of 0.12 degrees/min and step size of 0.020 degrees.

Sample was placed on Si zero-return ultra-micro sample holders. Analysis was performed using a 10 mm irradiated width and the following parameters were set within the hardware/software:

X-ray tube: Cu KV, 45 kV, 40 mA
Detector: X'Celerator
ASS Primary Slit: Fixed 1°
Divergence Slit (Prog): Automatic—5 mm irradiated length
Soller Slits: 0.02 radian
Scatter Slit (PASS): Automatic—5 mm observed length
Scan Range: 3.0-45.0°
Scan Mode: Continuous
Step Size: 0.02°
Time per Step: 10 s
Active Length: 2.54°
Following analysis the data was converted from adjustable to fixed slits using the X'Pert HighScore Plus software with the following parameters:
Fixed Divergence Slit Size: 1.00°, 1.59 mm
Crossover Point: 44.3° Omega In the Examples described below, unless otherwise specified, Compound 4 is the benzoyl protected compound.

Example 1

Preparation of N-(3,5-dichloro-4-((6-oxo-1,6-dihydropyridazin-3-yl)oxy)phenyl)benzamide (Compound 4 where $R^2$ is benzoyl)

A 1 L, three-neck, round-bottom flask equipped with overhead stirring, a thermocouple, reflux condenser, and $N_2$ inlet/outlet was charged with 3,6-dichloropyridazine (100 g, 0.672 mol, 1 wt), 4-amino-2,6-dichlorophenol (122 g, 0.686 mol, 1.02 equiv), and DMAC (500 mL, 5 vol). The resulting solution was charged with cesium carbonate (251 g, 0.771 mol, 1.15 equiv) and the suspension was heated to 110° C. After 3 h at that temperature, the batch temperature was lowered to 70° C. and stirred at that temperature for 16 h. $^1$H NMR analysis (DMSO) showed nearly all the dichloropyridazine had been consumed and the reaction was deemed complete. The batch was cooled to room temperature and transferred to a 3 L, round-bottom flask with the aid of EtOAc (2 L, 20 vol). Silica gel (100 g, 1 wt) was added and the suspension was agitated for 30 min and filtered. The reactor and cake were rinsed with EtOAc (500 mL, 5 vol) until the filtrate eluted colorless. The resulting filtrate was treated with 10% aqueous NaCl (2 L, 20 vol), the biphasic mixture was agitated for 30 min, and the lower aqueous layer was discarded. The upper organic layer was concentrated to dryness under reduced pressure. EtOAc (100 mL, 1 vol) was added to the residue and concentrated to dryness under reduced pressure to provide crude Compound 2 (251 g, 128% yield) as an oil. HPLC analysis showed a purity of 93.4%. $^1$H NMR analysis (DMSO) was consistent with the assigned structure and showed ≈25% DMAC and 2% EtOAc present.

Other conditions for synthesizing Compound 2 are described in Tables 1-3 below.

TABLE 1

Summary of Reaction Parameters for Compound 2

| Scale (g) | Conditions | % Yield | $^1$H NMR or HPLC |
|---|---|---|---|
| 5.0 | Int. 1 1 equiv<br>DMSO 5 vol<br>KOtBu 1.1 equiv<br>Int. 3 1 equiv<br>85° C. | 80 | ≈90% pure |
| 15 | Int. 1 1 equiv<br>DMSO 5 vol<br>KOtBu 1.1 equiv<br>Int. 3 1 equiv<br>85° C. | 84 | ≈90% pure |
| 15 | Int. 1 1 equiv<br>DMAC 5 vol<br>KOtBu 1.1 equiv<br>Int. 3 1 equiv<br>85° C. | 70 | ≈90% pure |
| 50.0 | Int. 1 0.98 equiv<br>DMAC 5 vol<br>KOtBu 1.1 equiv<br>Int. 3 1 equiv<br>85° C. | — | Telescoped |
| 17.45 | Int. 1 0.98 equiv<br>DMSO 5 vol<br>KOtBu 1.1 equiv<br>Int. 3 1 equiv<br>85° C. | 85 | ≈95% |

TABLE 2

Summary of Reaction Parameters for Compound 2

| Solvent | Conditions | Time (h) | % Yield | HPLC AUC (220 nm) | NMR Purity |
|---|---|---|---|---|---|
| DMSO | 1.15 + 0.26 equiv KOtBu<br>1 equiv Int. 1<br>1.02 equiv Int. 3<br>85° C. | 26 | 98 | 72.2 | Contains DMSO |
| DMAC | 1.15 equiv Cs$_2$CO$_3$<br>1 equiv Int. 1<br>1.02 equiv Int. 3<br>120° C. | 2 | 130 | 88.8 | Contains 33% DMAC |
| NMP | 1.15 equiv Cs$_2$CO$_3$<br>1 equiv Int. 1<br>1.02 equiv Int. 3<br>120° C. | 2 | 172 | 86.8 | Contains 46% NMP |
| DMAC | 1.0 equiv Cs$_2$CO$_3$<br>1 equiv Int. 1<br>1.02 equiv Int. 3<br>120° C. | 4 | 120 | 66.0 | Contains 42% DMAC |
| DMAC | 1.02 equiv 2<br>1.15 equiv Cs$_2$CO$_3$<br>5 vol DMAC<br>110° C. to 70° C. | 1<br>2.25<br>3.25<br>19 | 128 | 93.4% | Contains 26% DMAC 2% EtOAc |

TABLE 3

Summary of Reaction Parameters for Compound 2 (all reactions are in DMAC)

| Base | Time (h) | Temp. ° C. | HPLC IPC (220 nm) |
|---|---|---|---|
| Cs$_2$CO$_3$ | 3 | 110 | 94.8% |
|  | 15 | 90 | 94.4% |
| Li$_2$CO$_3$ | 3 | 110 | 12.7% |
| K$_2$CO$_3$ | 3 | 110 | 91.6% |
|  | 15 | 90 | 91.4% |
| Na$_2$CO$_3$ | 3 | 110 | 84.5% |
|  | 15 | 90 | 84.9% |
| NaOAc | 3 | 110 | 25.2% |
| KF | 3 | 110 | 54.1% |
| DIPEA | 3 | 110 | 22.8% |
| DBU | 3 | 110 | 80.8% |
|  | 15 | 90 | — |
| DABCO | 3 | 110 | 6.2% |
| KOH (ground) | 3 | 110 | 85.1% |

The crude 2 above was taken up in acetic acid (1.48 L, 7.5 vol) and benzoic anhydride (168 g, 0.741 mol, 1.1 equiv) was added. The resulting mixture was heated to 100° C. and after 35 min at that temperature, the amount of 2 was 0.8%. Sodium acetate (110 g, 2 equiv) was added and the temperature increased to 110° C. After 14.5 h at that temperature, HPLC analysis of the reaction mixture showed no intermediate remaining, and the reaction was deemed complete. The batch was cooled to 75° C. and water (1.5 L, 7.7 vol) was added over a period of 1 hour while maintaining a batch temperature between 72-75° C. The batch was cooled to 21° C. and filtered through Sharkskin filter paper. The reactor and cake were washed sequentially with water (1 L, 5 vol). After drying the collected solid in a 50° C. vacuum oven for 16 h, the yield of crude 4 was 195 g (77%). HPLC analysis (Method B, 220 nm) showed a purity of 91.6%.

| HPLC method B: |
|---|
| Column: Waters Sunfire C18, 3.5 μM, 4.6 × 150 mm |
| Flow rate: 1.0 mL/min. |
| Mobile phase A: 0.05% TFA in water |
| Mobile phase B: 0.05% TFA in H$_2$O |
| Diluent: 50:50 MeCN/H$_2$O |

| Time (min.) | % A | % B |
|---|---|---|
| 0.0 | 98 | 2 |

-continued

| HPLC method B: | | |
|---|---|---|
| 5.0 | 98 | 2 |
| 20 | 5 | 95 |
| 25 | 5 | 95 |
| 25.1 | 98 | 2 |
| 30 | 98 | 2 |

$^1$H NMR analysis (DMSO) was consistent with the assigned structure and indicated an acetic acid content of 1%. Benzoyl chloride was also used for the protection instead of benzoic anhydride. When benzoyl chloride was used, bases such as cesium carbonate or potassium carbonate were used and the reaction was carried out at room temperature.

Other conditions for synthesizing Compound 4 are described in Tables 4 and 5 below.

TABLE 4

Protection/hydrolysis of Compound 2 (Yields Reported from Int. 1)
(benzoyl protecting group)

| Solvent | Conditions | Time (h) | IPC % Pdt | % Yield | HPLC Purity (% AUC) |
|---|---|---|---|---|---|
| Acetic acid | 1. 1.03 equiv2<br>1.15 equiv Cs$_2$CO$_3$<br>3 vol DMSO<br>2. Bz$_2$O<br>3. Acetic acid, 115° C. | 1. 2 h<br>2. 19 h<br>3. 20.5 h | 1. 70<br>2. 70.7<br>3. 68.8 | 71 | 78.2 |
| Acetic acid | 1.1 equiv Bz$_2$O<br>2 equiv NaOAc<br>110° C. | 16.5 | 79.0 | 66 | 91.6 |
| Acetic acid | 1.1 equiv Bz$_2$O<br>2 equiv NaOAc<br>100-110° C. | 14.25 | 76.6 | 77 | 91.6 |

TABLE 5

Summary of Reaction Parameters for Compound 4 (acetate protecting group)

| Scale (g) | Conditions | % Yield | $^1$H NMR or HPLC |
|---|---|---|---|
| 5.0 | NaOAc 2 equiv<br>Acetic acid 4 vol<br>115° C. | 76 | ≈95% |
| 15.0 | NaOAc 2 equiv<br>Acetic acid 4 vol<br>115° C. | 60 | >99% |
| 50.0 g<br>(Int. 1) | NaOAc 2 equiv<br>Acetic acid 4 vol<br>115° C. | 51<br>2-step | ≈95% |

Purification of Compound 4: A 5 L, three-neck, round-bottom flask equipped with overhead stirring, a thermocouple, reflux condenser, and N$_2$ inlet/outlet was charged with crude 4 (100 g, 1 wt) and acetic acid (2 L, 20 vol). The slurry was agitated and heated to 95° C., and dissolution occurred. Water (2 L, 20 vol) was added over a period of 2.75 h while maintaining a batch temperature of ≈95° C., and precipitation occurred. The resulting slurry was heated at 95° C. for another 30 min before heating was removed. After the batch reached ambient temperature, it was stirred at that temperature overnight for convenience and filtered through Sharkskin filter paper. The reactor and cake were rinsed sequentially with water (1 L, 10 vol). The collected white solid was dried in a 40° C. vacuum oven to a constant weight of 91 g (91%). HPLC analysis of the dried solid showed a purity of 98.0%. $^1$H NMR analysis (DMSO) was consistent with the assigned structure and showed an acetic acid content of 0.3%. Table 6 below lists other conditions for purifying Compound 4.

TABLE 6

Purification of Compound 4 (R$^2$ = Bz)

| Solvent | Conditions | Time (h) | % Yield | HPLC Purity (% AUC) |
|---|---|---|---|---|
| Acetic acid/<br>H$_2$O | 1 equiv 4<br>20 vol AcOH<br>20 vol water<br>88-100° C. | 1 | 90 | 96.8 |
| Acetic acid/<br>H$_2$O | 1 equiv 4<br>20 vol AcOH<br>20 vol water<br>95° C. | 3 | 91 | 98.0 |
| Acetic acid/<br>H$_2$O | 1 equiv 4<br>20 vol AcOH<br>20 vol water<br>95° C. | 4 | 92 | 98.0 |
| Acetic acid/<br>H$_2$O | 1 equiv 4<br>12 vol AcOH<br>10 vol water<br>100-110° C. | 1 | 90 | 98.9 |

Example 2

Preparation of 6-(4-amino-2,6-dichlorophenoxy)-4-isopropylpyridazin-3(2H)-one (Int. 7)

A 4 L, four-neck, round-bottom flask equipped with overhead stirring, a thermocouple, N$_2$ inlet/outlet, and a reflux condenser was charged with 4 (95 g, 0.253 mol, 1 wt), THF (665 mL, 7 vol), and LiCl (32.3 g, 0.759 mol, 3 equiv). The resulting suspension was heated to 35° C., and isopropenylmagnesium bromide solution (0.5 M in THF, 1.72 L, 0.859 mol, 3.4 equiv) was added over a period of 80 min while maintaining a batch temperature between 35-45° C. After heating the resulting slurry at 40° C. for 3 h, HPLC analysis showed a conversion of 87%). Additional isopropenylmagnesium bromide solution (0.5 M in THF, 51 mL, 0.026 mol, 0.1 equiv) was added and the slurry was agitated at 40-43° C. for another 90 min. HPLC analysis showed a conversion of 92.9% and the reaction was deemed complete. The heating was removed, the reaction mixture was cooled to 14° C., and 3 N aqueous HCl (380 mL, 4 vol) was added slowly over 15 min while maintaining a batch temperature below 26° C., after which time all solids had dissolved. The lower aqueous layer was removed and extracted with THF (350 mL, 3.7 vol). After removing the lower aqueous layer, the combined organic layers were concentrated under reduced pressure to approximately 5 vol with respect to 4. The resulting solution was charged with 10% (w/w) aqueous KOH (532 mL, 5.6 vol), and the mixture was heated to 85° C. while distilling off THF using a short-path distillation apparatus. The batch was held at 85° C. for 11 h, and the heating was removed. The batch was cooled to ambient temperature overnight for convenience. HPLC analysis (Method A below) of the resulting slurry showed a conversion of 99% to Int. 7 and the reaction was deemed complete.

| HPLC method A |
| --- |
| Column: Waters Sunfire C18, 3.5 µM, 4.6 × 150 mm |
| Flow rate: 1.0 mL/min. |
| Mobile phase A: 0.05% TFA in water |
| Mobile phase B: 0.05% TFA in H$_2$O |
| Diluent: 50:50 MeCN/H$_2$O |

| Time (min.) | % A | % B |
| --- | --- | --- |
| 0.0 | 98 | 2 |
| 15.0 | 5 | 95 |
| 25 | 5 | 95 |
| 25.1 | 98 | 2 |
| 30 | 98 | 2 |

The batch temperature was adjusted to 48° C. and 3 N aqueous HCl (152 mL, 1.6 vol) was added over 35 min to adjust the pH to 7.5-8.0 while maintaining a batch temperature of 46-48° C. Heating was removed and the slurry was cooled to 30° C. $^1$H NMR analysis (DMSO) showed an Int. 7/THF mol ratio of 1.0:0.22 (Attachment 14). The batch was filtered at 30° C. through Sharkskin filter paper and the reactor and cake were washed with water (475 mL, 5 vol) sequentially. The beige solid Int. 7 was dried in a 40° C. vacuum oven to a constant weight of 81.6 g (102% yield). Karl Fischer analysis indicated a water content of 0.8%. $^1$H NMR (DMSO) was consistent with the assigned structure and indicated a THF content of 0.4%. HPLC analysis showed a purity of 92.6%. Tables 7-10 below provide summaries of reaction parameters for producing Int. 7.

TABLE 7

Summary of Grignard Isopropenylation Runs

| Scale (g) | Conditions | % Yield | $^1$H NMR or HPLC |
| --- | --- | --- | --- |
| 5.0 | 1 equiv 4<br>7 vol THF<br>3.4 equiv Grignard<br>3 equiv LiCl<br>40° C. | 97 | 94.1 |
| 25.0 | 1 equiv 4<br>7 vol THF<br>3.4 equiv Grignard<br>3 equiv LiCl<br>40° C. | 102 | 93.1 |
| 95.5 | 1 equiv 4<br>7 vol THF<br>3.5 equiv Grignard<br>3 equiv LiCl<br>40° C. | 101 | 92.6 |
| 5.0 | 1 eq 4<br>3 eq LiCl<br>8 vol THF<br>3.4 eq Grignard<br>1.5M in MeTHF<br>40° C. | 97 | 90.7 |
| 5.0 | 1 eq 4<br>3 eq LiCl<br>15 vol THF<br>2 eq t-BuMgCl<br>2M in THF<br>1.7 eq Grignard<br>1.5M in MeTHF<br>40° C. | 100 | 87.5 |
| 5.0 | 1 eq 4<br>3 eq LiCl<br>15 vol THF<br>3.6 eq Grignard<br>0.5M in THF<br>40° C. | 90 | 86.9 |
| 10.0 | 1 eq 4<br>3 eq LiCl<br>13 vol THF | 114 | 85.4 |

TABLE 7-continued

Summary of Grignard Isopropenylation Runs

| Scale (g) | Conditions | % Yield | $^1$H NMR or HPLC |
| --- | --- | --- | --- |
|  | 3.7 eq Grignard<br>1.5M in MeTHF<br>40° C. |  |  |
| 10.0 | 1 eq 4<br>3 eq LiBr<br>13 vol THF<br>3.7 eq Grignard<br>1.5M in MeTHF<br>40° C. | 67 | 89.3 |
| 10.0 | 1 eq 4<br>5 eq LiCl<br>13 vol THF<br>3.7 eq Grignard<br>0.5M in THF<br>40° C. | 88 | 91.2 |

TABLE 8

Summary of Grignard Isopropylation Runs

| Scale (g) | Conditions | % Yield | $^1$H NMR or HPLC |
| --- | --- | --- | --- |
| 1.0 | 1 equiv 4 (R$^2$ = Ac)<br>20 vol THF<br>3.3 equiv iPrMgCl<br>30° C. | 35 | >95 |
| 5.0 | 1 equiv 4 (R$^2$ = Ac)<br>20 vol THF<br>6 equiv iPrMgCl<br>40° C. | 94 | ≈90 |
| 2.0 | 1 equiv 4<br>20 vol THF<br>4 equiv iPrMgCl<br>20° C. | 51 | >95 |
| 1.21 | 1 equiv 4<br>20 vol Dioxane<br>4.1 equiv iPrMgCl<br>40° C. | — | — |
| 2.0 | 1 equiv 4 (R$^2$ = Ac)<br>8 equiv iPrMgCl<br>30 vol THF<br>25-42° C. | — | — |
| 1.1 | 1 equiv 4<br>2 equiv LiCl<br>4 equiv iPrMgCl<br>27 vol THF | — | Telescoped into oxidation |
| 1.0 | 1 equiv 4 (R$^2$ = Ac)<br>3 equiv LiCl<br>5 equiv iPrMgCl<br>25 vol THF | — | — |
| 2.0 | 1 equiv 4<br>3 equiv LiCl<br>4 equiv iPrMgCl<br>10 vol THF | 46 | >95 |
| 4.0 | 1 equiv 4<br>3 equiv LiCl<br>4.1 equiv iPrMgCl<br>7 vol THF | 95 | 88 |
| 5.0 | 1 equiv 4<br>3 equiv LiCl<br>3.5 equiv iPrMgCl<br>7 vol THF | — | Telescoped into oxidation |
| 10.0 | 1 equiv 4<br>3 equiv LiCl<br>3.2 equiv iPrMgCl<br>7 vol THF | — | Telescoped into oxidation |
| 5.0 | 1 equiv 4<br>3 equiv LiCl<br>3.4 equiv iPrMgCl<br>10 vol THF | — | Telescoped into oxidation |
| 5.0 | 1 equiv 4<br>3 equiv LiCl | — | Telescoped into |

TABLE 8-continued

Summary of Grignard Isopropylation Runs

| Scale (g) | Conditions | % Yield | $^1$H NMR or HPLC |
|---|---|---|---|
| | 3.4 equiv iPrMgCl 10 vol THF | | oxidation |

TABLE 9

Summary of the Bromine Oxidation of Pyridazinone Compound 5

| Scale (g) | Conditions | % Yield | $^1$H NMR or HPLC |
|---|---|---|---|
| 0.13 | 5 ($R^2$ = Ac) 1 equiv<br>$Br_2$ 2 equiv<br>AcOH 10 vol<br>90° C. | 82 | ≈95% |
| 3.09 | 5 ($R^2$ = Ac) 1 equiv<br>$Br_2$ 1.5 equiv<br>AcOH 7 vol<br>90° C. | 84 | ≈80% |
| 0.82 | 5 ($R^2$ = Bz) 1 equiv<br>$Br_2$ 1.5 equiv<br>AcOH 7 vol<br>90° C. | 84 | >95% |
| 1.1 | 5 ($R^2$ = Bz) 1 equiv<br>AcOH 10 vol<br>$Br_2$ 5 equiv<br>90° C. | 86<br>2-step | ≈90<br>2-step |
| 1.02 | 5 ($R^2$ = Bz) 1 equiv<br>AcOH 10 vol<br>$Br_2$ 1.5 equiv<br>90° C. | 100 | ≈95 |
| 1.55 | 5 ($R^2$ = Bz) 1 equiv<br>AcOH 10 vol<br>$Br_2$ 1.5 equiv<br>60° C. | 103<br>2-step | 89.6<br>2-step |
| 1.71 | 5 ($R^2$ = Bz) 1 equiv<br>AcOH 10 vol<br>$Br_2$ 1.5 equiv<br>60° C. | 84<br>2-step | 91.9 |

TABLE 10

Summary of Deprotection of Compound 6 to obtain Int. 7

| Protecting group | Conditions | Temp | Time (h) | Conversion (% AUC) |
|---|---|---|---|---|
| Acetyl | TFA (10 vol)<br>Water (10 vol) | 90° C. | 15<br>61 | 21.6<br>19.9 |
| Bz (benzoyl) | TFA (10 vol)<br>Water (10 vol) | 90° C. | 15<br>61 | 40.1<br>100 |
| Bz | $BF_3$•$Et_2O$ (6 equiv)<br>MeOH (10 vol)<br>Add water (10 equiv) | RT<br>60° C.<br>60° C. | 15<br>4.5<br>18 | NR<br>13.0<br>31.1 |
| Bz | 6N KOH (10 vol) | 90° C. | 16 | 100 |
| Bz | 2N NaOH (5 vol) | RT<br>60° C. | 5.5<br>16 | 4.7<br>31.2 |
| | 2N NaOH (2.5 vol) | RT | 5.5 | 6.1 |
| Bz | MeOH (2.5 vol) | 60° C. | 16 | 40.3 |
| Bz | $Na_2CO_3$ (10 wt %, 5 vol) | 70° C. | 2 | 7.0 |
| Bz | KOH (10 wt %, 5 vol) | 70° C. | 2<br>23<br>52 | 19.6<br>86.9<br>97.3 |

Example 3

Preparation of (Z)-ethyl(2-cyano-2-(2-(3,5-dichloro-4-((5-isopropyl-6-oxo-1,6-dihydropyridazin-3-yl)oxy)phenyl)hydrazono)acetyl)carbamate (Int. 8)

A 2 L, three-neck, round-bottom flask equipped with overhead stirring, a thermocouple, $N_2$ inlet/outlet was charged with Int. 7 (75.0 g, 0.239 mol, 1 wt), acetic acid (600 mL, 8 vol), water (150 mL, 2 vol), and concentrated HCl (71.3 mL, 0.95 vol). The resulting thin slurry was cooled to 6° C. and a solution of $NaNO_2$ (16.8 g, 0.243 mol, 1.02 equiv) in water (37.5 mL, 0.5 vol) was added over a period of 10 min while maintaining a batch temperature below 10° C. After an additional 10 min of agitation between 5-10° C., HPLC analysis showed complete conversion of Int. 7 to the diazonium intermediate. A solution of NaOAc (54.5 g, 0.664 mol, 2.78 equiv) in water (225 mL, 3 vol) was added over a period of 6 min while maintaining a batch temperature below 10° C. N-cyanoacetylurethane (37.9 g, 0.243 mol, 1.02 equiv) was immediately added, the cooling was removed, and the batch naturally warmed to 8° C. over 35 min. HPLC analysis showed complete consumption of the diazonium intermediate and the reaction was deemed complete. The batch warmed naturally to 21° C. and was filtered through Sharkskin filter paper. The reactor and cake were washed sequentially with water (375 mL, 5 vol) twice. The collected orange solid was dried in a 35° C. vacuum oven for 64 h to provide crude Int. 8 (104.8 g, 91%).

A 1 L, three-neck, round-bottom flask equipped with overhead stirring, a thermocouple, and $N_2$ inlet/outlet was charged with crude Int. 8 (104.4 g, 1 wt) and acetic acid (522 mL, 5 vol). The resulting slurry was heated to 50° C. and held at that temperature for 1.5 h. The batch cooled naturally to 25° C. over 2 h and was filtered through Sharkskin filter paper. The reactor and cake were washed sequentially with water (522 mL, 5 vol) and the cake conditioned under vacuum for 1.75 h. The light orange solid was dried to constant weight in a 40° C. vacuum oven to provide 89.9 g (78% from Int. 7) of the desired product. $^1$H NMR (DMSO) was consistent with the assigned structure.

Example 4

Preparation of 2-(3,5-dichloro-4-((5-isopropyl-6-oxo-1,6-dihydropyridazin-3-yl)oxy)phenyl)-3,5-dioxo-2,3,4,5-tetrahydro-1,2,4-triazine-6-carbonitrile (Compound A)

A 2 L, three-neck, round-bottom flask equipped with overhead stirring, a thermocouple, $N_2$ inlet/outlet, and reflux condenser was charged with Int. 8 (89.3 g, 0.185 mol, 1 wt), DMAC (446 mL, 5 vol), and KOAc (20.0 g, 0.204 mol, 1.1 equiv). The mixture was heated to 120° C. and held at that temperature for 2 h. HPLC analysis showed complete conversion to Compound A. The batch temperature was adjusted to 18° C. over 1 h, and acetic acid (22.3 mL, 0.25 vol) was added. The batch temperature was adjusted to 8° C., and water (714 mL, 8 vol) was added over 1 h; an orange slurry formed. The batch was filtered through Sharkskin filter paper and the cake was allowed to condition overnight under $N_2$ without vacuum for convenience. A premixed solution of 1:1 acetone/water (445 mL, 5 vol) was charged to the flask and added to the cake as a rinse with vacuum applied. After 2 h of conditioning the cake under vacuum, it was transferred to a clean 1 L, three-neck, round-bottom flask equipped with overhead stirring, a thermocouple, and $N_2$ inlet/outlet. Ethanol (357 mL, 4 vol) and acetone (357 mL, 4 vol) were charged and the resulting slurry was heated to 60° C.; dissolution occurred. Water (890 mL, 10 vol) was added over a period of 90 min while maintaining a batch temperature between 55-60° C. The resulting slurry was allowed to cool to 25° C. and filtered through Sharkskin filter paper. The reactor and cake were washed sequentially with a solution of 1:1 EtOH/water (446 mL, 5 vol). The cake was conditioned overnight under $N_2$ without vacuum for convenience. The cracks in the cake were smoothed and vacuum applied. The cake was washed with water (179 mL, 2 vol) and dried in a 45° C. vacuum oven to a constant weight of 70.5 g (87%, crude Compound A). HPLC analysis showed a purity of 94.8%.

A 500 mL, three-neck, round-bottom flask equipped with overhead stirring, a thermocouple, $N_2$ inlet/outlet, and reflux condenser was charged with crude Compound A (70.0 g) and MIBK (350 mL, 5 vol). The orange slurry was heated to 50° C. and held at that temperature for 2 h. The batch cooled naturally to 23° C. and was filtered through Sharkskin filter paper. The reactor and cake were washed sequentially with MIBK (35 mL, 0.5 vol) twice. The collected solids were dried in a 45° C. vacuum oven to a constant weight of 58.5 g (84%). This solid was charged to a 500 mL, three-neck, round-bottom flask equipped with overhead stirring, a thermocouple, $N_2$ inlet/outlet, and reflux condenser. Ethanol (290 mL, 5 vol) was added and the slurry was heated to reflux. After 3.5 h at reflux, XRPD showed the solid was consistent with Form I, and heating was removed. Upon reaching 25° C., the batch was filtered through filter paper, and the reactor and cake were washed sequentially with EtOH (174 mL, 3 vol). The tan solid Compound A was dried in a 40° C. vacuum oven to a constant weight of 50.4 g (87%, 64% from Int. 8). HPLC analysis showed a purity of 99.1%. $^1$H NMR (DMSO) was consistent with the assigned structure.

Example 5

Scaled up preparation of 2-(3,5-dichloro-4-((5-isopropyl-6-oxo-1,6-dihydropyridazin-3-yl)oxy)phenyl)-3,5-dioxo-2,3,4,5-tetrahydro-1,2,4-triazine-6-carbonitrile (Compound A)

A larger scale batch of Compound A was synthesized according to the scheme below. The conditions in the scheme below are similar to those described in Examples 1-4 above.

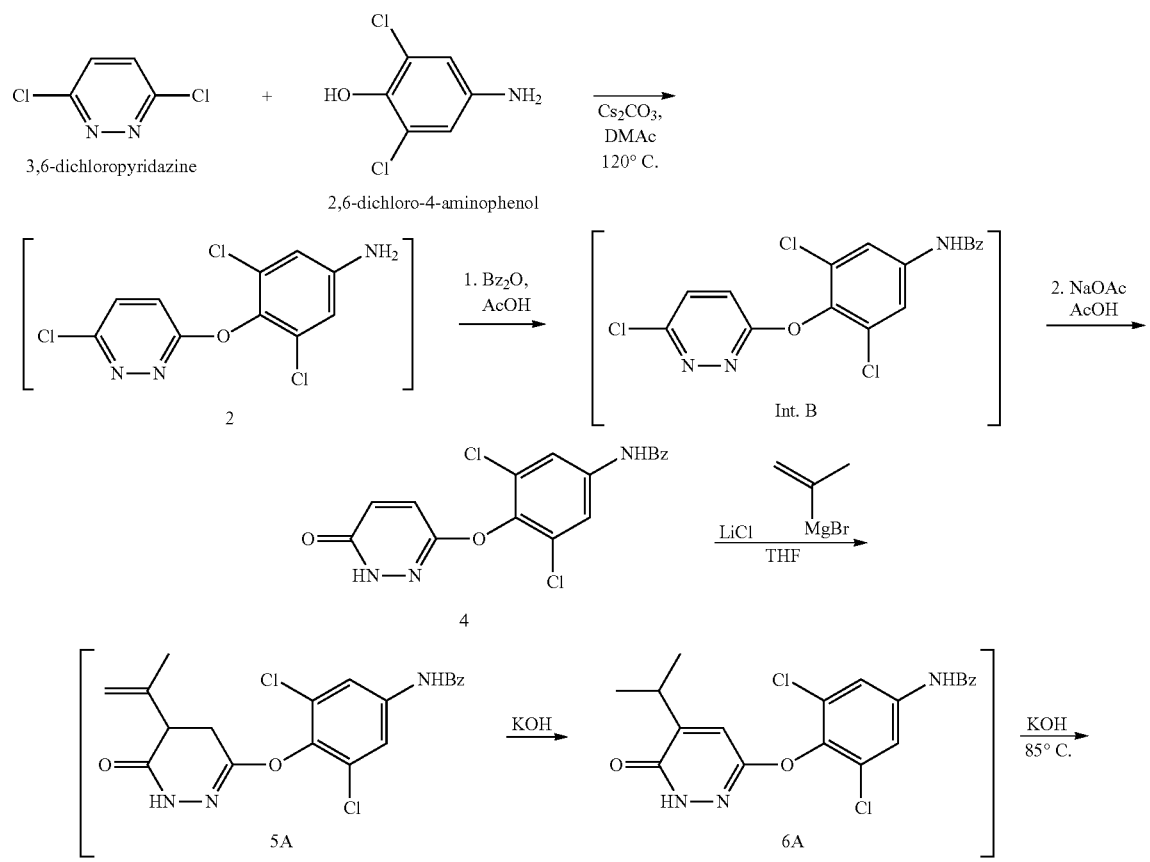

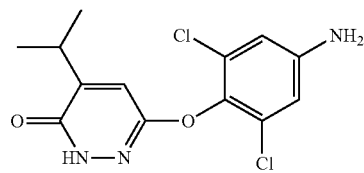

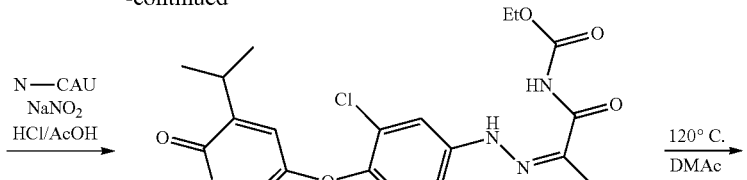

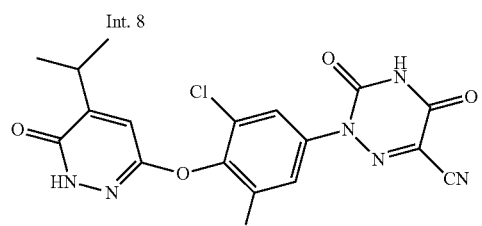

Compound A

Synthesis of 4

A 50 L jacketed glass vessel (purged with N₂) was charged with 3,6-dichloropyridazine (2.00 kg), 4-amino-2,6-dichlorophenol (2.44 kg) and N,N-dimethylacetamide (10.0 L). The batch was vacuum (26 inHg)/nitrogen (1 PSIG) purged 3 times. Cesium carbonate (5.03 kg) was added and the batch temperature was adjusted from 22.3° C. to 65.0° C. over 3.5 hours. The batch was held at 65.0° C. for 20 hours. At this point, ¹H NMR analysis indicated 3.34% 3,6-dichloropyridazine relative to 2. The batch temperature was adjusted to 21.5° C. and ethyl acetate (4.00 L) was added to the batch. The batch was agitated for 10 minutes and then filtered through a 18" Nutsche filter equipped with polypropylene filter cloth. The filtration took 15 minutes. Ethyl acetate (5.34 L) was charged to the vessel and transferred to the filter as a rinse. The batch was then manually re-suspended in the filter before re-applying vacuum. This process was repeated 2 more times and the filter cake was conditioned for 10 minutes. The filtrate was charged to a 100-L vessel that contained (16.0 L) of a previously prepared 15% sodium chloride in H₂O. The batch was agitated for 5 minutes and then allowed to separate for 35 minutes. The interface was not visible, so the calculated 23 L of the lower aqueous phase was removed. 16.0 L of 15% Sodium chloride in H₂O was added to the batch. The batch was agitated for 6 minutes and then allowed to separate for 7 minutes. The interface was visible at ~19 L and the lower aqueous phase was removed. 17.0 L of 15% Sodium chloride in H₂O was added to the batch. The batch was agitated for 7 minutes and then allowed to separate for 11 minutes. The lower aqueous phase was removed. The vessel was set up for vacuum distillation and the batch was concentrated from 17.0 L to 8.0 L over 2 hours 20 minutes with the batch temperature kept around 21° C. Benzoic anhydride (3.19 kg) and acetic acid (18.0 L) were charged to the vessel. The vessel was set up for vacuum distillation and the batch was concentrated from 28.0 L to 12.0 L over 2 days (overnight hold at 20° C.) with the batch temperature kept between 20 and 55° C. At this point, ¹H NMR analysis indicated a mol ratio of acetic acid to ethyl acetate of 1.0:0.015. Acetic acid (4.0 L) was charged to the batch and the batch was distilled to 12 L. ¹H NMR analysis indicated a mol ratio of acetic acid to ethyl acetate of 1.0: 0.0036. Acetic acid (20.0 L) was charged to the batch and the batch temperature was adjusted to 70.0° C. The batch was sampled for HPLC analysis and 2 was 0.16%. Sodium acetate (2.20 kg) was added to the batch and the batch temperature was adjusted from 72.4° C. to 110.0° C. After 18.5 hours, HPLC analysis indicated no Int. B detected. The batch temperature was adjusted from 111.3 to 74.7° C. and DI water (30.0 L) was added to the batch over 2 hours. The batch temperature was adjusted to 20.5° C. and then filtered using a 24" Haselloy Nutsche filter equipped with polypropylene filter cloth. A previously prepared solution of 1:1 acetic acid in DI H₂O (10.0 L) was charged to the vessel and agitated for 5 minutes. The wash was transferred to the filter and the batch was then manually re-suspended in the filter before re-applying vacuum. DI H₂O (10.0 L) was charged to the vessel and then transferred to the filter. The batch was manually re-suspended in the filter before re-applying vacuum. DI H₂O (10.0 L) was charged directly to the filter and the batch was then manually re-suspended in the filter before re-applying vacuum. The filter cake was allowed to condition for 18 hours to give 14.4 kg of 4. HPLC analysis indicated a purity of 93.7%. This wet cake was carried forward into the purification. A 100 L jacketed glass vessel (purged with N₂) was charged with crude 4 (wet cake 14.42 kg), acetic acid (48.8 L) and the agitator was started. DI H₂O (1.74 L) was charged. The batch (a slurry) temperature was adjusted from 18.1 to 100.1° C. over 4.25 hours. The batch was held at 100.1 to 106.1° C. for 1 hour and then adjusted to 73.1° C. DI H₂O (28.0 L) was added to the batch over 1 hour keeping the batch temperature between 73.1 and 70.3° C. The batch temperature was adjusted further from 70.3° C. to 25.0° C. overnight. The batch was filtered using a 24" Hastelloy Nutsche filter equipped with polypropylene filter cloth. The filtration took 13 minutes. A solution of DI H₂O (9.00 L) and acetic acid (11.0 L) was prepared and added to the 100 L vessel. The mixture was agitated for 5 minutes and then transferred to the filter cake. DI H₂O (20.0 L) was charged to the vessel, agitated for 6 minutes and then transferred to the filter cake. DI H₂O (20.0 L) was charged to the vessel, agitated for 9 minutes and then transferred to the filter cake. The batch was allowed to condition for 3 days and then transferred to drying trays for vacuum oven drying. After 3 days at 50° C. and 28"/Hg, the batch gave a 74% yield (3.7 kg) of 4 as an off-white solid. The ¹H NMR spectrum was consistent with the assigned structure, HPLC analysis indicated a purity of 98.87% and KF analysis indicated 0.14% H₂O.

Synthesis of Int. 7

A 100-L jacketed glass vessel (purged with N2) was charged with tetrahydrofuran (44.4 L). The agitator was started (125 RPM) and 4 (3.67 kg) was charged followed by lithium chloride (1.26 kg). The batch temperature was observed to be 26.7° C. and was an amber solution. Isopropenylmagnesium bromide 1.64 molar solution in 2-methyl THF (21.29 kg) was added over 2½ hours keeping the batch between 24.3 and 33.6° C. The batch was agitated at 24.5° C. for 17 hours at which point HPLC analysis indicated 9% 4. A 2nd 100-L jacketed glass vessel (purged with N2) was charged with 3N hydrogen chloride (18.3 L). The batch was transferred to the vessel containing the 3N HCl over 25 minutes keeping the batch temperature between 20 and 46° C. A bi-phasic solution was observed. The quenched batch was transferred back to the 1$^{st}$ 100-L vessel to quench the small amount of residue left behind. THF (2.00 L) was used as a rinse. The batch temperature was observed to be 40.9° C. and was agitated at 318 RPM for 45 minutes. The batch temperature was adjusted to 21.8° C. and the layers were allowed to separate. The separation took 10 minutes. The lower aqueous phase was removed (~26.0 L). A solution of sodium chloride (1.56 kg) in DI water (14.0 L) was prepared and added to the batch. This was agitated at 318 RPM for 10 minutes and agitator was stopped. The separation took 3 minutes. The lower aqueous phase was removed (~16.0 L). The batch was vacuum distilled from 58.0 L to 18.4 L using ~24"/Hg and a jacket temperature of 50 to 55° C. A solution of potassium hydroxide (2.30 kg) in DI water (20.7 L) was prepared in a 72-L round bottom flask. The vessel was set up for atmospheric distillation using 2 distillation heads and the batch was transferred to the 72-L vessel. THF (0.75 L) was used as a rinse. The batch volume was ~41.0 L, the temperature was adjusted to 64.1° C. and distillation started with the aid of a N2 sweep. Heating was continued to drive the batch temperature to 85.4° C. while distilling at which point the 72-L vessel was set up for reflux (batch volume was about 28.0 L at the end of the distillation). The batch was held at 85° C. for 13 hours at which point HPLC analysis indicated 0.3% compound 6A. Heating was stopped and the batch was transferred to a 100-L jacketed glass vessel. Solids were observed. The batch temperature was adjusted from 70.6° C. to 56.7° C. A previously prepared solution of sodium hydrogen carbonate (2.82 kg) in DI water (35.0 L) was added over 80 minutes keeping the batch temperature between 56.7 and 46.7° C. The batch pH at the end of the addition was 9.8. The batch was held at 46.7 to 49.0° C. for 40 minutes and then cooled to 25.0° C. The batch was filtered using a 18" stainless steel Nutsche filter. DI water (18.4 L) was charged to the vessel and transferred to the filter. The filter cake was manually re-suspended in the filter and then the liquors were removed. This process was repeated once more and the filter cake was 3" thick. The filter cake was conditioned on the filter for 3 days, was transferred to drying trays and dried in a vacuum oven at 45° C. to provide 2.93 kg Int. 7 (95% yield) with an HPLC purity of 87.6%.

Synthesis of Int. 8

A 100 L jacketed glass vessel (purged with N₂ and plumbed to a caustic scrubber) was charged with acidic acid (13.0 L). Int. 7 (2.85 kg) was charged to the vessel and the agitator was started. N-Cyanoacetylurethane (1.56 kg) and DI water (5.70 L) were charged to the vessel. The batch temperature was adjusted from 17.0° C. to 5.5° C. and a thin slurry was observed. At this point 37% hydrogen chloride (2.70 L) was added over 10 minutes keeping the batch temperature between 4.8° C. and 8.8° C. A previously prepared solution of sodium nitrite (638 g) in DI water (1.42 L) was added over 26 minutes keeping the batch temperature between 5.8° C. and 8.7° C. A brown gas was observed in the vessel head space during the addition. HPLC analysis indicated no Int. 7 detected. At this point a previously prepared solution of sodium acetate (2.07 kg) in DI water (8.50 L) was added over 47 minutes keeping the batch temperature between 5.5° C. and 9.5° C. After the addition, a thin layer of orange residue was observed on the vessel wall just above the level of the batch. The batch temperature was adjusted from 9.4° C. to 24.5° C. and held at 25° C. (±5° C.) for 12 hours. The batch was filtered using a 24" Hastelloy Nutsche filter equipped with tight-weave polypropylene filter cloth. The filtration took 30 minutes. The vessel was rinsed with 14.3 L of a 1:1 acidic acid/DI water. The orange residue on the reactor washed away with the rinse. The rinse was transferred to the filter where the batch was manually re-suspended. Vacuum was re-applied to remove the wash. A 2$^{nd}$ 1:1 acidic acid/DI water wash was performed as above and the batch was conditioned on the filter for 26 hours. HPLC analysis of the wet filter cake indicated purity was 90.4%. The batch was dried to a constant weight of 3.97 kg (91% yield) in a vacuum oven at 45° C. and 28"/Hg.

Preparation of Compound a DMAC Solvate

A 100 L, jacketed, glass vessel purged with N₂ was charged with Int. 8 (3.90 kg) and potassium acetate (875 g). N,N-dimethylacetamide (DMAC, 18.3 L) was charged to the vessel and the agitator was started. The batch temperature was adjusted to 115° C. over 2 h. After 2 h at 115° C., the batch was sampled and HPLC analysis indicated 0.27% Int. 8 remained. The batch temperature was adjusted to 25.0° C. overnight. Acetic acid (975 mL) was added to the batch and the batch was agitated further for 3 h. The batch was transferred to a carboy and the vessel was rinsed clean with 800 mL of DMAC. The batch was transferred back to the 100 L vessel using vacuum through a 10 μm in-line filter and a DMAC rinse (1.15 L) was used. The filtration was fast at the beginning but slow at the end, plugging up the filter. The batch temperature was adjusted to 11.1° C. and DI water (35.1 L) was added over 2 h 20 min, keeping the batch temperature between 5-15° C. The batch was held for 1 h and filtered, using an 18" Nutsche filter equipped with tight-weave polypropylene cloth. The filtration took 15 h. A 1:1 ethanol/DI water wash (19.5 L) was charged to the vessel, cooled to 10° C., and transferred to the filter cake. The cake was allowed to condition under N₂ and vacuum for 8 h and transferred to drying trays. The batch was dried in a vacuum oven at 45° C. and 28"/Hg to give 89% yield (3.77 kg) of Compound A DMAC solvate as an orange/tan solid. The ¹H NMR spectrum was consistent with the assigned structure and Karl Fischer analysis indicated 0.49% H₂O. XRPD indicated the expected form, i.e., Compound A DMAC solvate. Thermogravimetric analysis (TGA) indicated 16% weight loss. HPLC analysis indicated a purity of 93.67%.

Preparation of Crude Compound A

A 100 L, jacketed, glass vessel purged with N₂ was charged with Compound A DMAC solvate (3.75 kg) and ethanol (15.0 L). The agitator was started and acetone (15.0 L) was added. The batch temperature was adjusted from 10.6° C. to 60.0° C. over 1 h. At this point, the batch was in solution. DI water was added to the batch over 1.5 h, keeping the batch temperature at 60±5° C. The batch was held at 60±5° C. for 1 h and cooled to 23.5° C. An 18" Nutsche filter equipped with tight-weave (0.67 CFM) polypropylene cloth was set up and the batch was filtered. The filtration took 15 h. A 1:1 ethanol/DI water wash (19.5 L) was charged to the vessel and transferred to the filter cake. The cake was allowed to condition under $N_2$ and vacuum for 8 h and transferred to drying trays. The batch was dried in a vacuum oven at 45° C. and 28"/Hg for five days to give a 94% yield (2.90 kg) of Compound A as a powdery tan solid. The $^1$H NMR spectrum is consistent with the assigned structure and Karl Fischer analysis indicated 6.6% $H_2O$. XRPD indicated the expected form of dihydrate. TGA indicated 6.7% weight loss. HPLC analysis indicated a purity of 96.4% (AUC).

Purification of Crude Compound A

A 50 L, jacketed, glass vessel purged with $N_2$ was charged with Compound A crude (2.90 kg) and methyl isobutyl ketone (14.5 L). The agitator was started and the batch temperature was adjusted from 20.2° C. to 50.4° C. over 1.5 h. The batch was held at 50° C. (±5° C.) for 1 h and cooled to 20-25° C. The batch was held at 20-25° C. for 2.5 h. An 18" Nutsche filter equipped with tight-weave (0.67 CFM) polypropylene cloth was set up and the batch was filtered. The filtration took 20 min. Methyl isobutyl ketone (MIBK, 1.45 L) was charged to the vessel and transferred to the filter cake. The cake was manually resuspended and the liquors were pulled through with vacuum. Methyl isobutyl ketone (2.90 L) was charged to the filter cake and the cake was manually resuspended. The liquors were pulled through with vacuum and the cake was conditioned with vacuum and nitrogen for 15 h. The filter cake dried into a tan, hard 18"×1½" disc. This was manually broken up and run through coffee grinders to give a 76% yield (2.72 kg) of MGL-3196 MIBK solvate as a tan, powdery solid. No oven drying was necessary. The $^1$H NMR spectrum was consistent with the assigned structure and Karl Fischer analysis indicated <0.1% $H_2O$. XRPD indicated the expected form MIBK solvate. TGA indicated 17.3% weight loss. HPLC analysis indicated a purity of 98.5%.

Example 6

Conversion of Compound A to Form I

Purified Compound A (4802 g) as a 1:1 MIBK solvate which was obtained from Int. 8 as described in Example 5 above was added into a jacketed, 100 L reactor along with 24 liters of ethanol. The resulting slurry was heated to 80±5° C. (reflux) over 1 h 25 min; the mixture was stirred at that temperature for 4 h 25 min. Analysis of the filtered solids at 2 h 55 min indicated that the form conversion was complete, with the XRPD spectra conforming to Form I. The mixture was cooled to 20±5° C. over 45 min and stirred at that temperature for 15 min. The slurry was filtered and the filter cake was washed twice with prefiltered ethanol (2×4.8 L). The wet cake (4.28 kg) was dried under vacuum at 40±5° C. for 118 h to afford 3390 g of Compound A form I.

The X-ray Powder Diffraction study was performed on different lots of Compound A morphic Form I generated by the process described above. XRPD after micronization confirms Form 1.

The data for Form I is provided in Table 11 below and the diffractograms of Form I are provided as FIG. 1.

TABLE 11

| 2θ (angle) | d value (Å) | Intensity (counts) | Intensity % (%) |
|---|---|---|---|
| 3.0288 | 29.17117 | 1925.62 | 15.89 |
| 3.4596 | 25.5397 | 832.08 | 4.58 |
| 3.6702 | 24.07429 | 707.65 | 3.89 |
| 4.0027 | 22.07529 | 410.45 | 6.78 |
| 4.4466 | 19.87232 | 432.4 | 2.38 |
| 4.5794 | 19.29632 | 429.89 | 4.73 |
| 5.2533 | 16.82257 | 320.41 | 5.29 |
| 5.8566 | 15.09082 | 335.71 | 1.85 |
| 6.05 | 14.60887 | 224.56 | 9.89 |
| 6.8068 | 12.98624 | 287.97 | 3.17 |
| 7.2152 | 12.25213 | 293.93 | 4.04 |
| 7.6426 | 11.56781 | 239.85 | 2.64 |
| 8.2256 | 10.74918 | 1637.27 | 13.51 |
| 8.8542 | 9.98745 | 309.91 | 3.41 |
| 9.115 | 9.70221 | 244.6 | 2.02 |
| 9.576 | 9.23622 | 255.43 | 2.11 |
| 10.5373 | 8.39569 | 9763.54 | 100 |
| 11.1868 | 7.9096 | 2398.13 | 24.56 |
| 13.0814 | 6.76802 | 164.19 | 3.36 |
| 13.9013 | 6.37063 | 197.28 | 1.52 |
| 14.3022 | 6.19296 | 290.11 | 2.23 |
| 14.7284 | 6.01469 | 94.1 | 0.96 |
| 15.7399 | 5.63037 | 1305.28 | 16.71 |
| 16.4002 | 5.40513 | 804.24 | 10.3 |
| 16.732 | 5.2987 | 173.26 | 2.22 |
| 17.3055 | 5.12435 | 145.15 | 2.97 |
| 17.6872 | 5.01461 | 1400.39 | 17.93 |
| 18.3399 | 4.83761 | 1233.01 | 9.47 |
| 18.6986 | 4.7456 | 9825.6 | 100 |
| 18.9598 | 4.6808 | 572.69 | 3.5 |
| 19.3018 | 4.59864 | 278.53 | 1.7 |
| 19.6643 | 4.51468 | 97.55 | 0.4 |
| 20.0939 | 4.41912 | 64.71 | 2.63 |
| 21.0604 | 4.21845 | 333.65 | 2.72 |
| 22.2097 | 4.00268 | 833.43 | 8.48 |
| 22.6128 | 3.93224 | 1304.95 | 10.62 |
| 22.8964 | 3.88417 | 3375.42 | 34.35 |
| 23.066 | 3.856 | 976.63 | 5.96 |
| 23.5742 | 3.77401 | 3115.33 | 38.05 |
| 23.8662 | 3.72849 | 571.62 | 4.65 |
| 24.1 | 3.69284 | 572.34 | 6.99 |
| 24.5243 | 3.62991 | 1097.27 | 6.7 |
| 24.6502 | 3.61166 | 1580.95 | 16.09 |
| 25.4993 | 3.49329 | 225.6 | 2.76 |
| 26.4933 | 3.36443 | 506.03 | 5.15 |
| 26.7528 | 3.33239 | 244.51 | 1.99 |
| 27.1244 | 3.28756 | 130.69 | 1.06 |
| 27.4354 | 3.251 | 546.35 | 4.45 |
| 27.8382 | 3.20487 | 213.44 | 2.17 |
| 28.5208 | 3.12971 | 158.82 | 1.29 |
| 28.9064 | 3.08883 | 436.59 | 2.67 |
| 29.1352 | 3.06509 | 710.53 | 5.79 |
| 29.5077 | 3.02724 | 416.16 | 4.24 |
| 30.0267 | 2.97608 | 1470.29 | 17.96 |
| 30.3658 | 2.94361 | 260.89 | 1.59 |
| 30.6326 | 2.91858 | 132.13 | 0.54 |
| 31.316 | 2.85644 | 177.78 | 1.45 |
| 31.6013 | 2.83129 | 397.61 | 5.67 |
| 31.9237 | 2.80343 | 514.26 | 4.19 |
| 32.2125 | 2.77895 | 1293.04 | 18.42 |
| 32.8721 | 2.72469 | 434.37 | 2.65 |
| 33.3755 | 2.68474 | 295.36 | 2.4 |
| 33.8232 | 2.65022 | 358.99 | 3.65 |
| 34.8364 | 2.57542 | 140.57 | 1.72 |
| 35.1838 | 2.55079 | 739.55 | 7.53 |
| 35.7301 | 2.51303 | 98.13 | 1.2 |
| 36.0084 | 2.49424 | 110.57 | 1.35 |
| 36.4676 | 2.46389 | 316.07 | 2.57 |
| 37.2747 | 2.41237 | 199.99 | 4.07 |
| 38.3543 | 2.34691 | 34.08 | 0.42 |
| 39.1941 | 2.29854 | 63.88 | 1.3 |
| 39.9663 | 2.25589 | 211.73 | 1.29 |
| 40.6489 | 2.21957 | 96.61 | 0.59 |
| 41.194 | 2.19145 | 167.45 | 1.36 |
| 42.0276 | 2.14989 | 47.01 | 0.57 |
| 42.4477 | 2.12958 | 290.42 | 1.77 |
| 42.8091 | 2.11244 | 200.71 | 1.63 |

TABLE 11-continued

| 2θ (angle) | d value (Å) | Intensity (counts) | Intensity % (%) |
|---|---|---|---|
| 43.6289 | 2.07463 | 171.28 | 2.09 |

Figure 2:
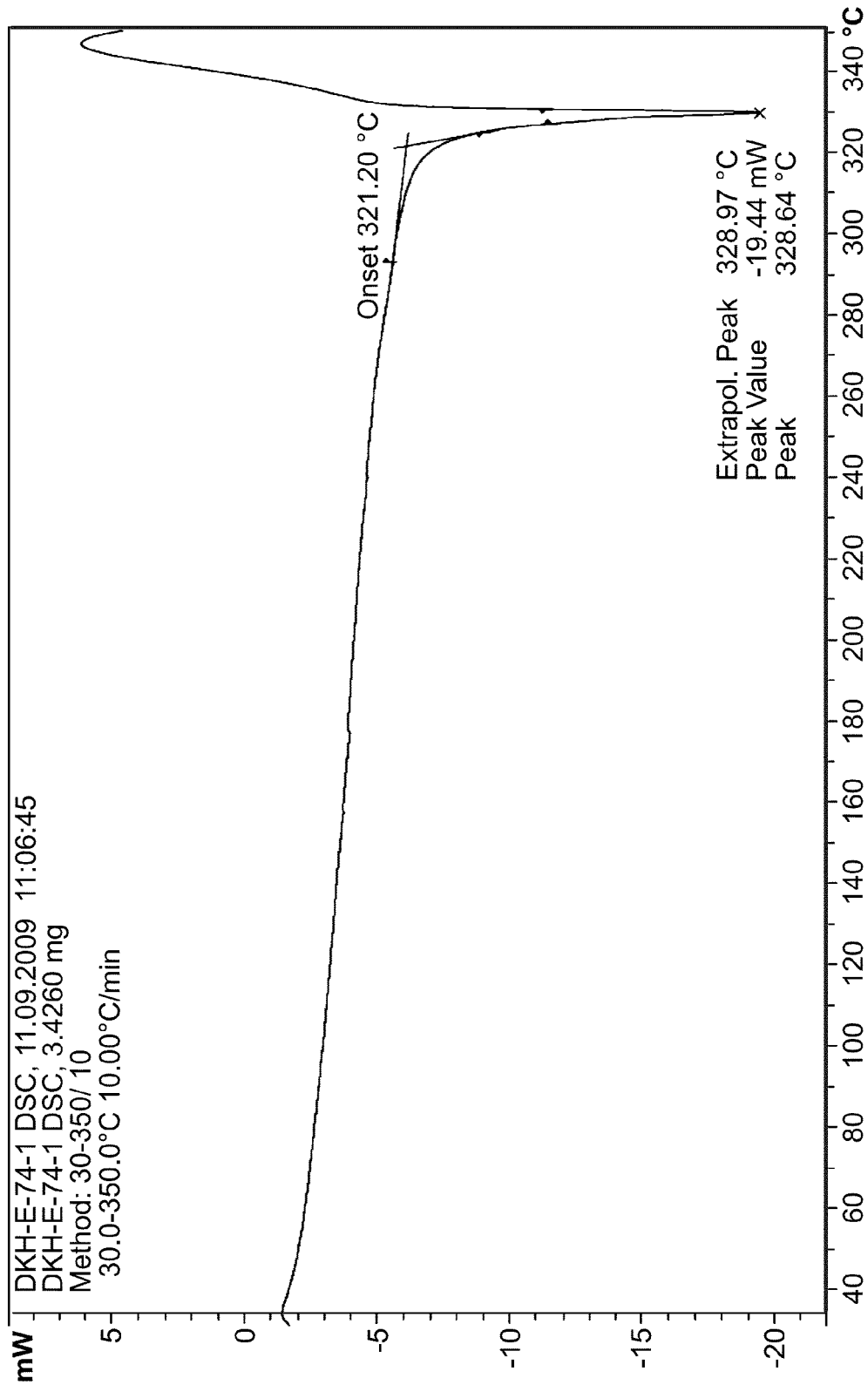
FIG. 2 is a differential scanning calorimetry (DSC) diagram of Compound A Form I.
Figure 3A:
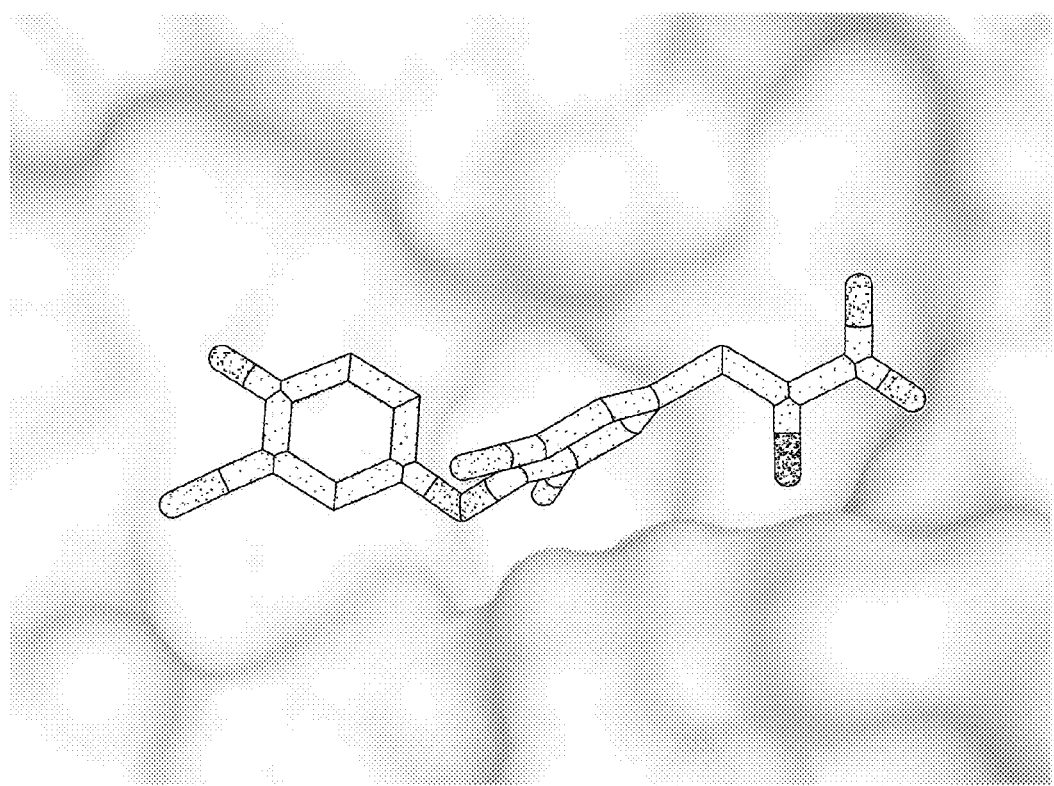
FIGS. 3A and 3B are MacPymol modeling images to show T3 and Compound A in THRβ, respectively.
Figure 3B:
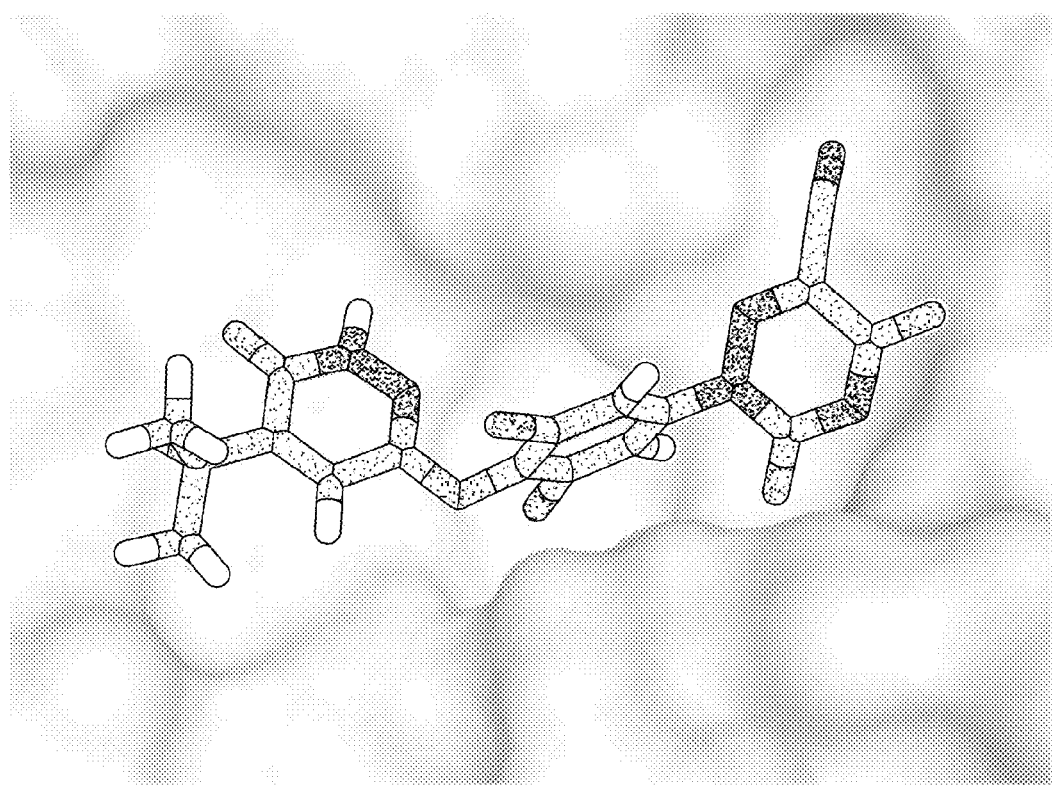
Figure 4:
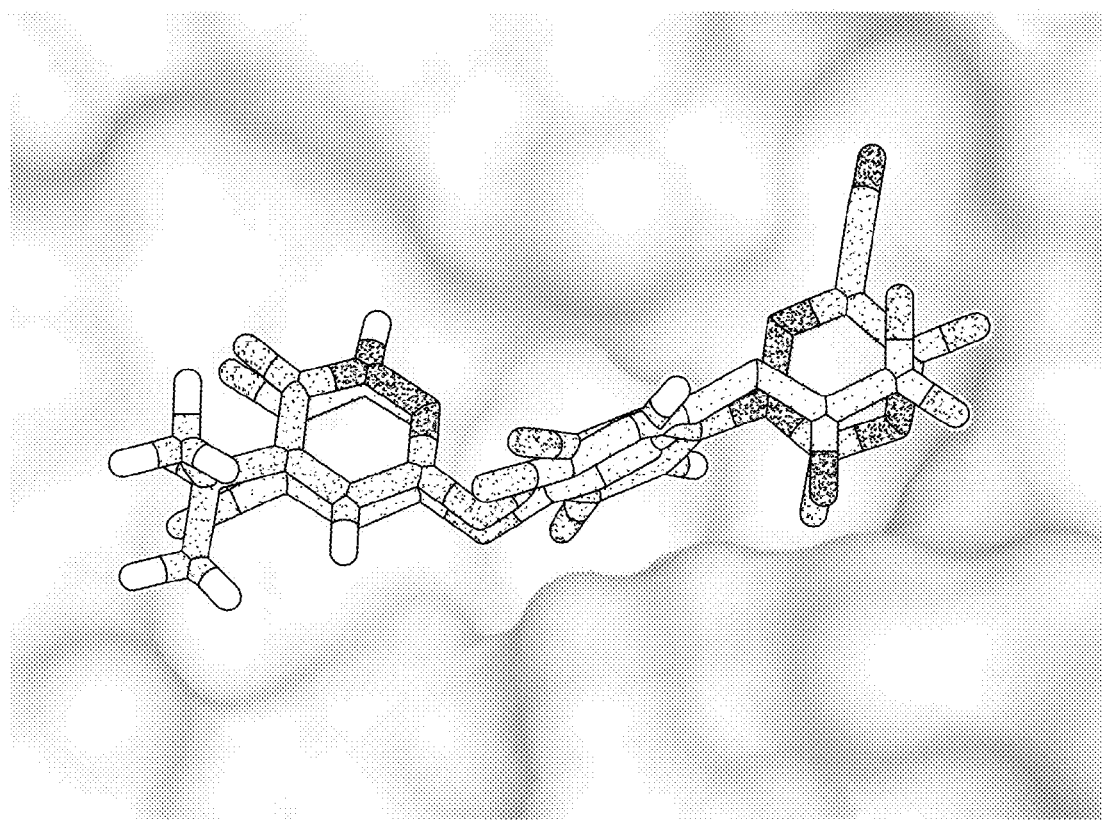
FIG. 4 is a MacPymol modeling image to show superimposed T3 and Compound A in THRβ.
Figure 5A:
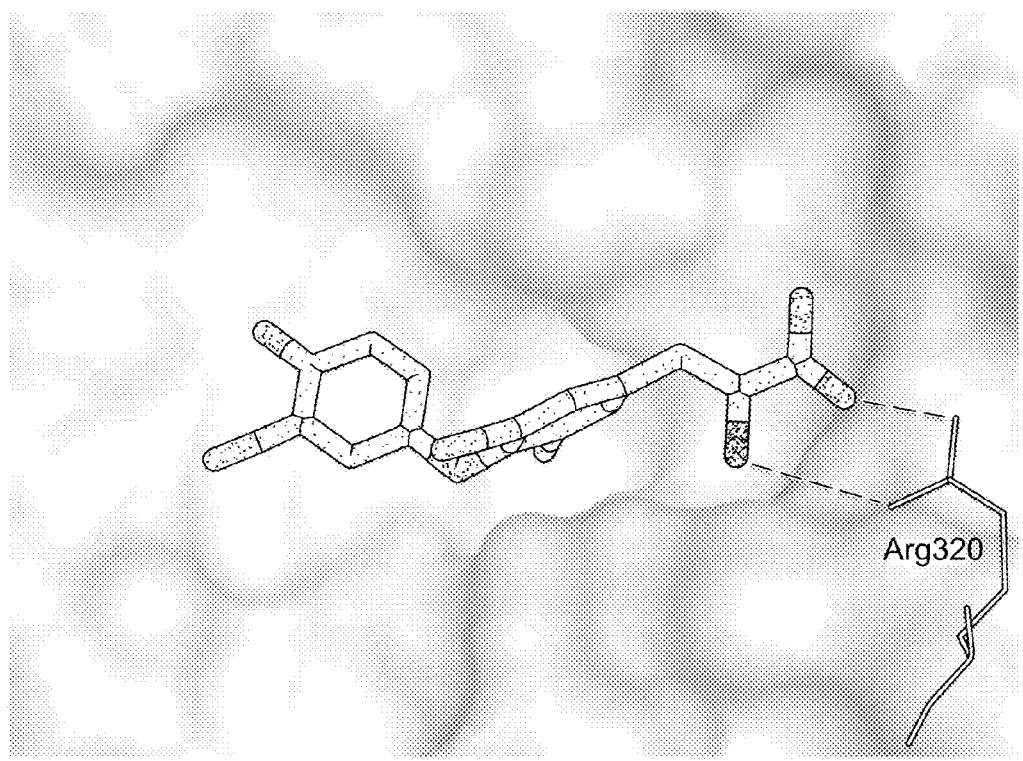
FIG. 5A is a MacPymol modeling image to show polar interactions between T3 and wild type THRβ, where T3 interacts with Arg320 very specifically.
Figure 5B:
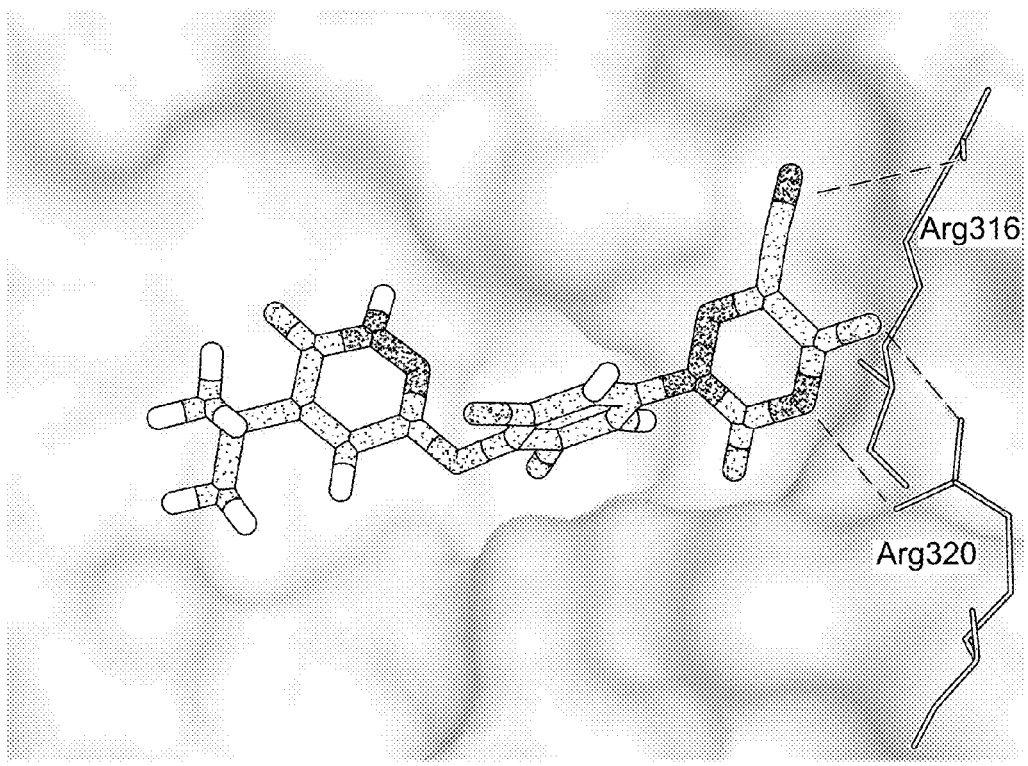
FIG. 5B is a MacPymol modeling image to show polar interactions between Compound A and wild type THRβ, where Compound A interacts with Arg320 and Arg316.
Figure 6:
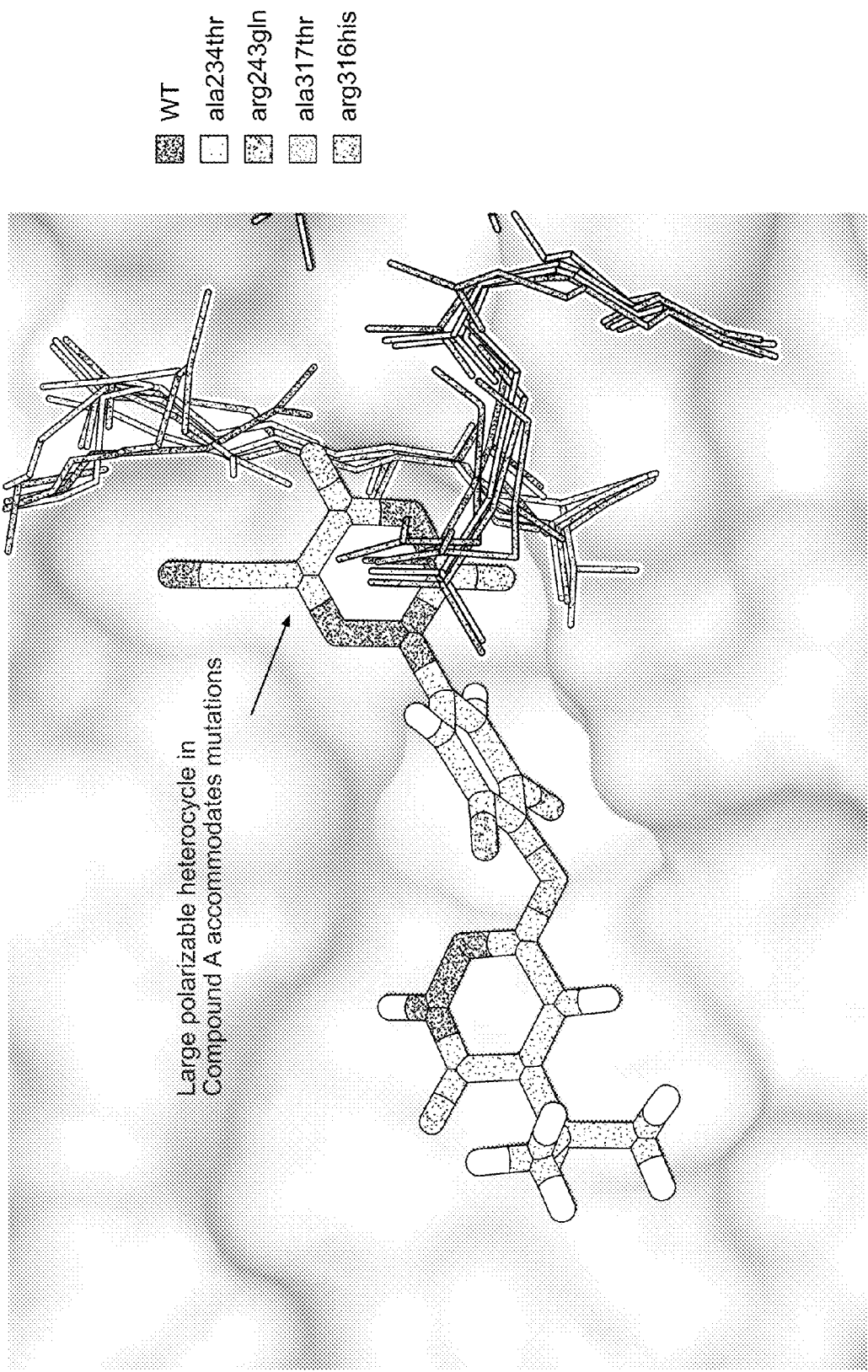
FIG. 6 is a MacPymol modeling image to show that mutations lead to many changes in the polar region of the ligand binding domain ("LBD").
Figure 7A:
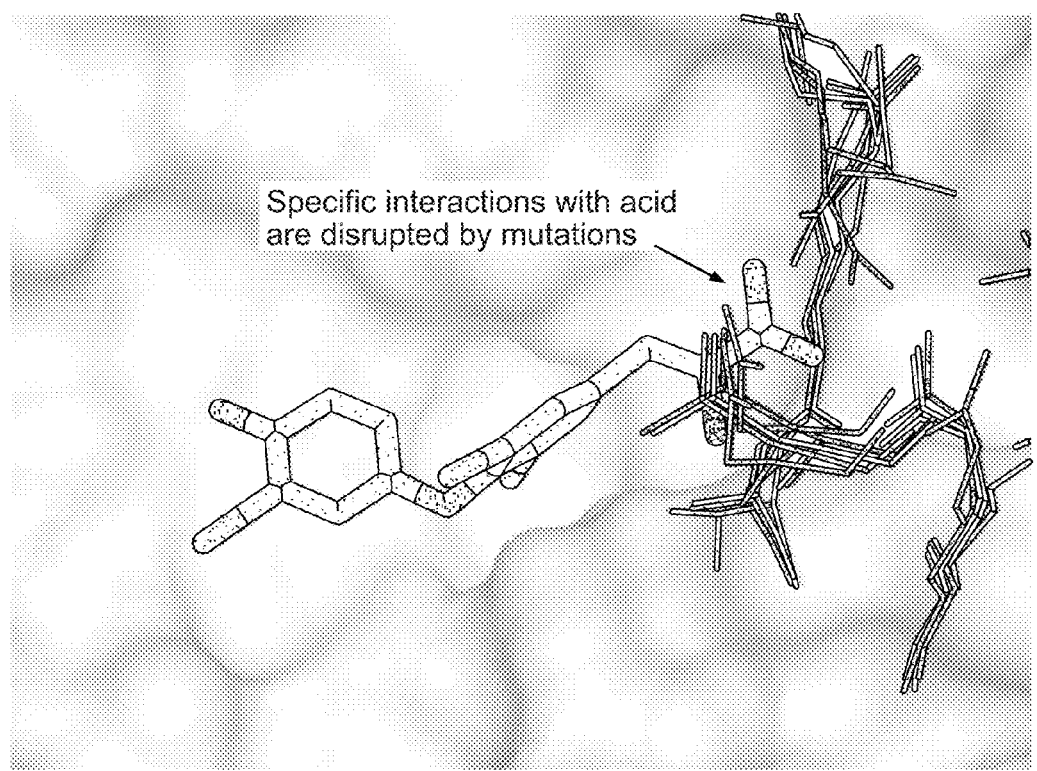
FIG. 7A is a MacPymol modeling image to show interactions between T3 and THRβ mutants: Ala234Thr, Arg243Gln, Arg316His, Ala317Thr.
Figure 7B:
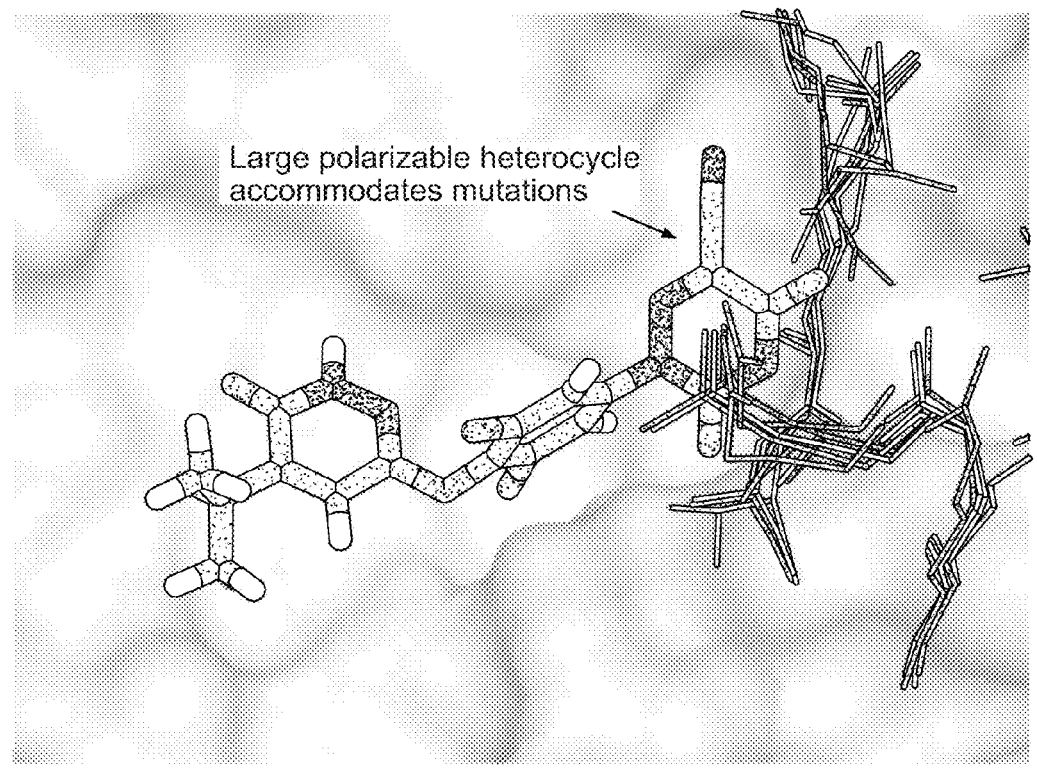
FIG. 7B is a MacPymol modeling image to show interactions between Compound A and THRβ mutants: Ala234Thr, Arg243Gln, Arg316His, Ala317Thr; indicating that, compared to T3, the negatively charged heterocycle in Compound A accommodates mutations better.

Form I was found to have a melting onset around 321° C., followed by decomposition upon melting by DSC (FIG. 2).

Example 7

Preparation of Compound A Form I: Conversion of Compound A Solvate to Form I

A 50 L, jacketed, glass vessel purged with $N_2$ was charged with Compound A MIBK solvate (2.72 kg) from Example 5 above and ethanol (13.6 L). The agitator was started and the batch temperature was adjusted from 16.8° C. to 79.4° C. over 1.3 h. The batch was held at 79.5° C. for 2 h and sampled for XRPD analysis. XRPD indicated Form I, and the batch was cooled to 24.9° C. over 1 h and 10 min. An 18" Nutsche filter equipped with tight-weave (0.67 CFM) polypropylene cloth was set up and the batch was filtered. The filtration took 4 min. Ethanol (2.8 L) was charged to the vessel and transferred to the filter cake. The cake was manually resuspended and the liquors were pulled through with vacuum. Ethanol (2.80 L) was charged to the filter cake and the cake was manually resuspended. The liquors were pulled through with vacuum and the cake was conditioned with vacuum and nitrogen for 1 h. The filter cake was transferred to drying pans and dried at 45° C. and 28"/Hg for one day to give an 89% yield (1.96 kg) of Compound A as a light yellow solid. HPLC analysis indicated a purity of 99.6%. XRPD analysis is consistent with Form I. Micronization of 300 g of this material on a 2" jet mill gave 284 g (95% yield) of micronized Compound A. XRPD analysis confirmed that micronized Compound A remained Form I.

Compound A DMAC solvate can be converted, via the dihydrate and the MIBK solvate, to Form I as described in Example 7. Alternatively, the DMAC solvate was converted directly to Form I in 75% yield (yield calculated from Intermediate 8) by heating it with 8 volumes of ethanol to 80° C. for 2 hours followed by cooling to room temperature and filtering. In another reaction, a sample of Compound A that was a mixture of the DMAC solvate and dihydrate was converted to Form I in 69% yield by heating it with 8 volumes of MIBK to 80° C. followed by cooling to room temperature.

Modeling of Interaction Between Compound a and Thyroid Hormone Receptor

Figure 8A:
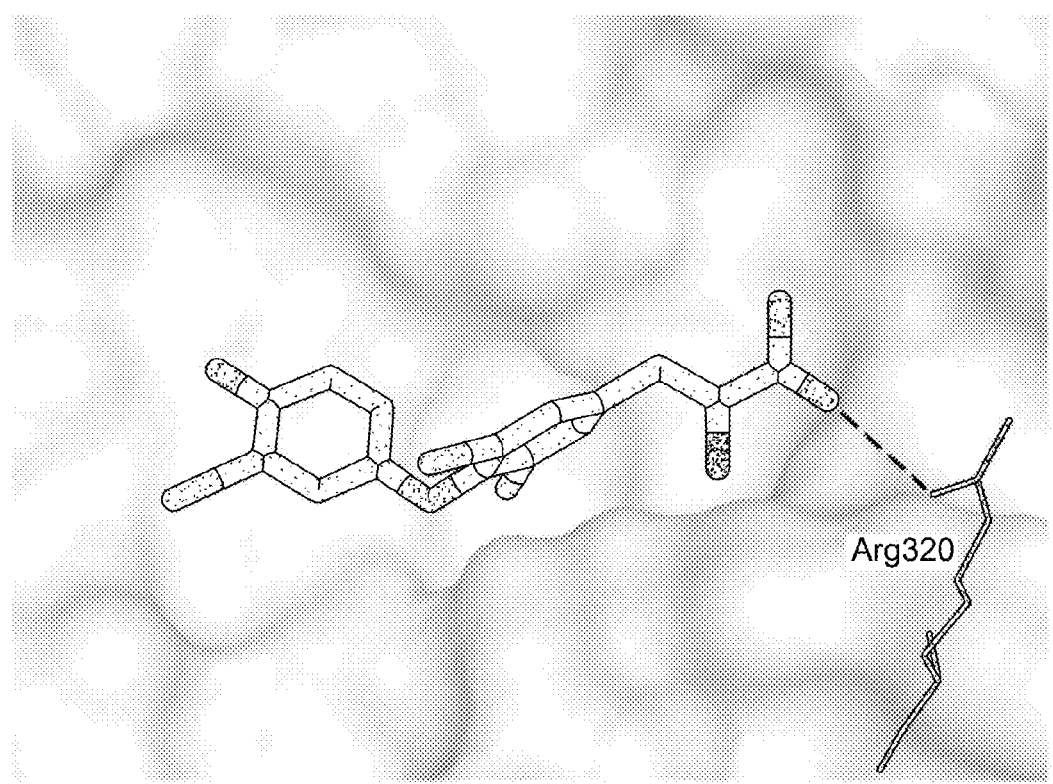
FIGS. 8A and 8B are MacPymol modeling images of T3 and Compound A in Arg316His mutant, respectively. T3-Arg320 interaction is likely weaker due to rotation of Arg320 away from ligand in the mutant, while Compound A maintains favorable interaction with Arg320 and is well positioned for the CN group to form a pi-cation interaction with the mutated His316.
Figure 8B:
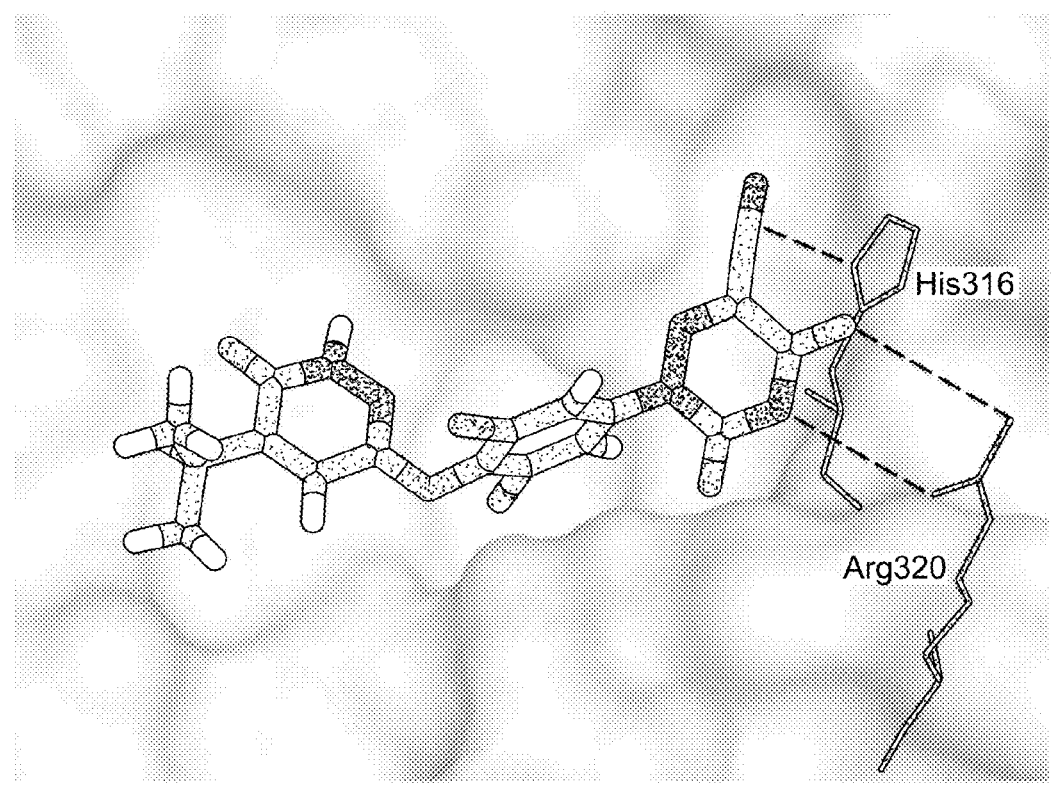
Figure 9A:
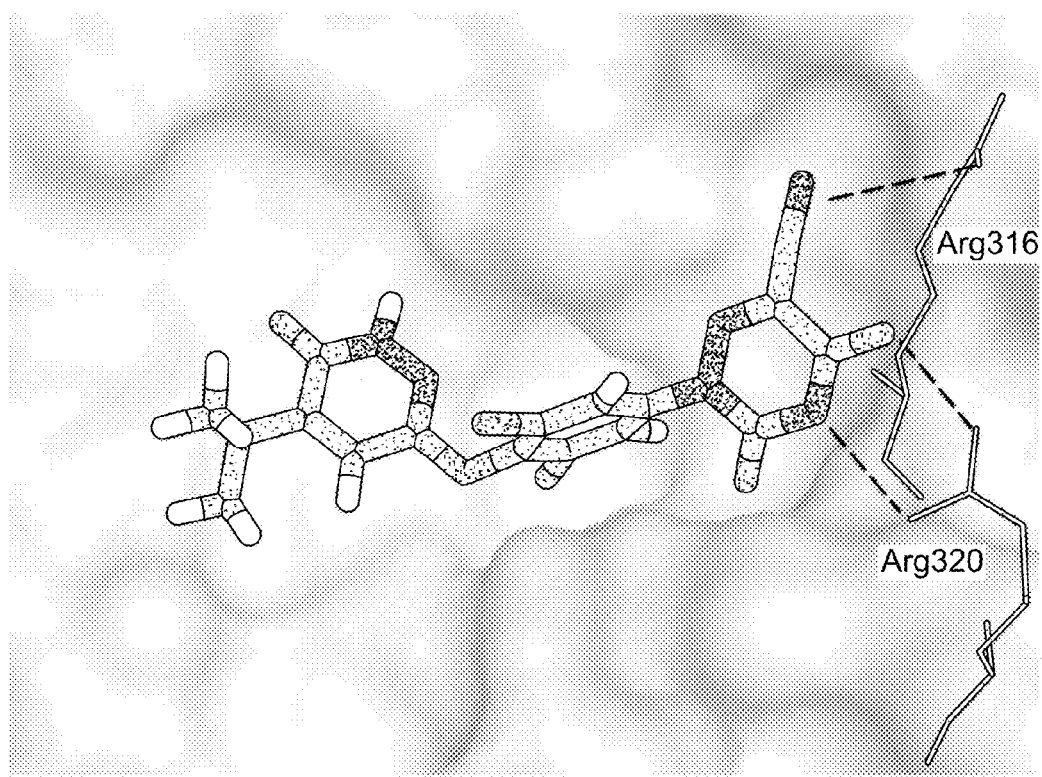
FIGS. 9A and 9B are MacPymol modeling images of Compound A in the WT THRβ and mutant Arg316His, respectively.
Figure 9B:
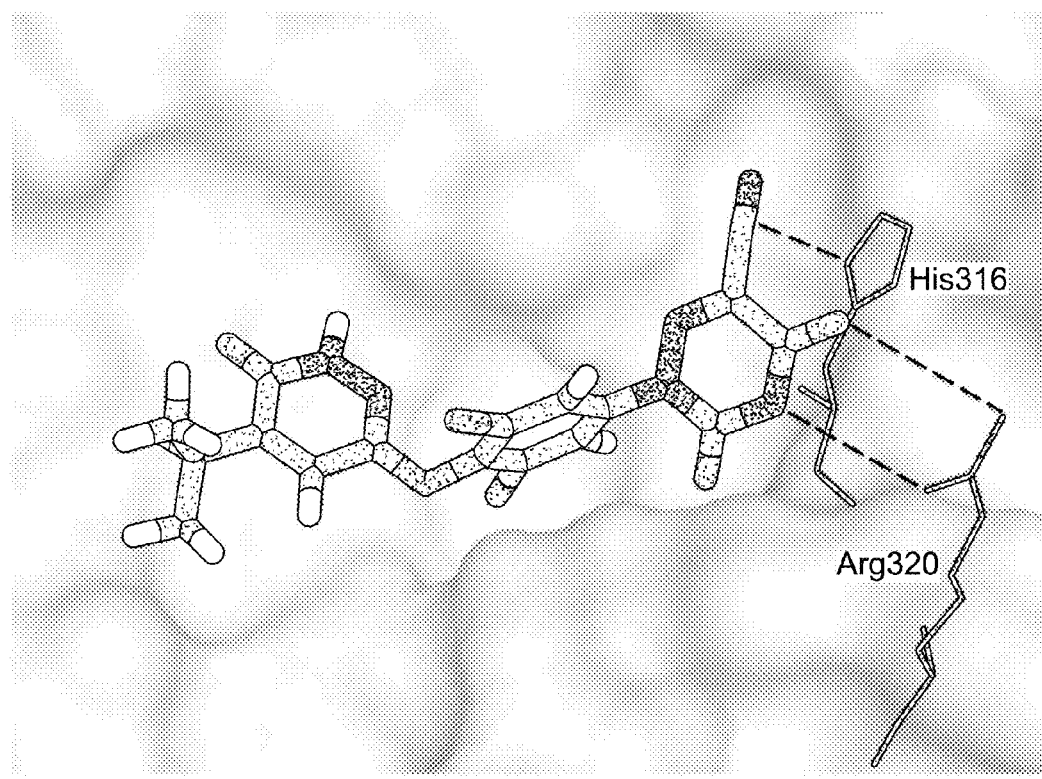

Crystal structures were obtained from the RCSB protein data bank (ID numbers: 1N46, 1NQ0, 1NQ1, 1NQ2 and 1NUO). The protein co-crystal structures were aligned using MacPymol for Mac OS X (Copyright 2006 DeLano Scientific LLC.; now a product of Schrodinger Inc.) MacPymol was also used for all analysis of the ligand-protein interactions and to render the FIGS. 3-9. These figures indicate that, overall, Compound A is better able to accommodate the structural variations in the THRβ mutants. For example, in mutant Arg316His, Arg316 is mutated to His and Arg320 is slightly shifted away from ligand. As a result, the specific interaction between Arg320 and T3 is less optimal in Arg316His mutant. In comparison, the large negative polarizable heterocycle in Compound A forms favorable interactions that are not disrupted by Arg316His mutation. In other words, Compound A, having a larger, more polarizable heterocycle, maintains favorable interactions with Arg320 and mutated His316. See, e.g., FIGS. 8 and 9. Results are similar for other mutations.

The table below lists the biochemical properties of certain TRβ mutants. Other mutants and their properties can be found in e.g., M. Adams et al., J Clin Invest. 1994; 94(2): 506-515, B. R. Huber et al., Mol Endocrinol, 2003, 17(4):643-652; and B. R. Huber et al., Mol Endocrinol, 2003, 17(1):107-116, the contents of each of which are hereby incorporated by reference in their entireties.

| TRβ | % T3 binding | Trans-Activation | Clinical |
|---|---|---|---|
| WT | 100 | 1X | Normal |
| Ala234Thr | High in solution, low in presence of thyroid response element DNA | .1X (normal at high T3) | |
| Arg243Gln | High in solution, severe decrease in presence of thyroid response element DNA | <.1X (normal at very high T3) | |
| Ala317Thr | 13 | Normal at 10XT3 | General resistance to thyroid hormone |
| Arg316His | .9 | Normal at high T3 | General resistance to thyroid hormone |

Equivalents

The invention can be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. A morphic form of 2-(3,5-dichloro-4-((5-isopropyl-6-oxo-1,6-dihydropyridazin-3-yl)oxy)phenyl)-3,5-dioxo-2,3,4,5-tetrahydro-1,2,4-triazine-6-carbonitrile ("Compound A") (Form I) characterized by an X-ray powder diffraction pattern including peaks at about 10.5, 18.7, 22.9, 23.6, and 24.7 degrees 2θ.

2. The morphic form of claim 1 characterized by an X-ray powder diffraction pattern further including peaks at about 8.2, 11.2, 15.7 16.4, 17.7, 30.0, and 32.2 degrees 2θ.

3. The morphic form of claim 1 characterized by an X-ray powder diffraction pattern substantially similar to that set forth in FIG. 1.

4. The morphic form of claim 1, wherein the morphic form has a purity of 95% or greater.

5. A pharmaceutical composition comprising a morphic form of claim 1 and a pharmaceutically acceptable carrier.

6. A synthetic process comprising:
(a) contacting $R^1MgX$ or $R^1Li$ with a compound of Formula (I):

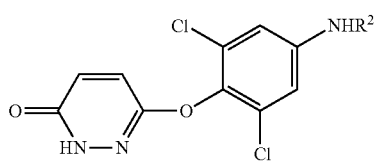

to form a compound of Formula (II):

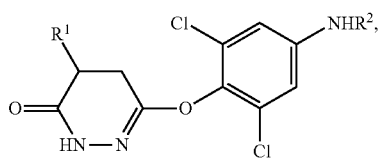

in which $R^1$ is isopropyl or isopropenyl, X is halo and $R^2$ is H or an amine protecting group; and
(b) converting the compound of Formula (II) to a compound of Formula (III):

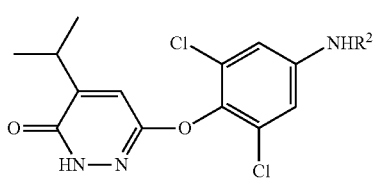

in the presence of a base when $R^1$ is isopropenyl or in the presence of an oxidizing agent when $R^1$ is isopropyl.

7. The process of claim 6, further comprising: (c), when present, removing the amine protecting group $R^2$ of the compound of Formula (III) to form 6-(4-amino-2,6-dichlorophenoxy)-4-isopropylpyridazin-3(2H)-one.

8. The process of claim 6, wherein step (a) is performed by contacting $R^1MgX$ with the compound of Formula (I), in which $R^1$ is isopropenyl and X is Br; or step (a) is performed by contacting $R^1MgX$ with the compound of Formula (I), in which $R^1$ is isopropyl and X is Cl.

9. The process of claim 6, wherein the oxidizing agent in step (b) is bromine and step (b) is performed in the presence of an acid.

10. The process of claim 6, wherein $R^2$ is acetyl or benzoyl.

11. The process of claim 7, further comprising: (d) converting 6-(4-amino-2,6-dichlorophenoxy)-4-isopropylpyridazin-3(2H)-one to 2-(3,5-dichloro-4-((5-isopropyl-6-oxo-1,6-dihydropyridazin-3-yl)oxy)phenyl)-3,5-dioxo-2,3,4,5-tetrahydro-1,2,4-triazine-6-carbonitrile ("Compound A") by contacting 6-(4-amino-2,6-dichlorophenoxy)-4-isopropylpyridazin-3(2H)-one with ethyl (2-cyanoacetyl)carbamate and a metal nitrite followed by treatment with potassium acetate in DMAC.

12. A process of preparing the preparing the morphic form of claim 1, the process comprising:
heating a mixture comprising a solvent and Compound A at a first temperature, and
cooling the mixture to a second temperature that is lower than the first temperature so as to obtain the morphic form of claim 1, wherein the solvent is selected from ethanol, isopropanol, methyl isobutyl ketone and a combination thereof.

13. The process of claim 12, wherein the first temperature is between about 60° C. and about 80° C.

14. The process of claim 12, wherein the second temperature is between about 0° C. and about 60° C.

15. The process of claim 12, wherein the solvent is ethanol or methyl isobutyl ketone.

16. A process of preparing a morphic form of claim 1, the process comprising:
heating a mixture comprising a solvent and Compound A at a first temperature, wherein the solvent is selected from ethanol, isopropanol, methyl isobutyl ketone and a combination thereof;
cooling the mixture to a second temperature that is lower than the first temperature;
filtering the mixture to obtain a filter cake;
rinsing the filter cake with an organic solvent to obtain a rinsed filter cake; and
drying the rinsed filter cake to obtain the morphic form of claim 1.

17. A process of preparing a morphic form of claim 1, the process comprising:
heating a mixture comprising ethanol and Compound A at a first temperature;
cooling the mixture to a second temperature that is lower than the first temperature but greater than about 40° C.;
filtering the mixture at a temperature not lower than about 40° C. to obtain a filter cake;
rinsing the filter cake at a temperature not lower than about 40° C. with ethanol to obtain a rinsed filter cake; and
drying the rinsed filter cake at a temperature not lower than about 40° C. to obtain the morphic form of claim 1.

* * * * *

UNITED STATES PATENT AND TRADEMARK OFFICE
CERTIFICATE OF CORRECTION

PATENT NO. : 9,266,861 B2  
APPLICATION NO. : 14/660720  
DATED : February 23, 2016  
INVENTOR(S) : D. Keith Hester, II et al.

Page 1 of 1

It is certified that error appears in the above-identified patent and that said Letters Patent is hereby corrected as shown below:

In the Claims

At Column 53, Claim number 2, Line number 16, replace:
"8.2, 11.2, 15.7 16.4, 17.7, 30.0, and 32.2 degrees 2θ."
With:
--8.2, 11.2, 15.7, 16.4, 17.7, 30.0, and 32.2 degrees 2θ.--

Signed and Sealed this  
Twentieth Day of August, 2019

Andrei Iancu  
*Director of the United States Patent and Trademark Office*

SEQUENCE LISTING

<160> NUMBER OF SEQ ID NOS: 2

<210> SEQ ID NO 1
<211> LENGTH: 259
<212> TYPE: PRT
<213> ORGANISM: Homo sapiens

<400> SEQUENCE: 1

Glu Leu Gln Lys Ser Ile Gly His Lys Pro Glu Pro Thr Asp Glu Glu
1               5                   10                  15

```
Trp Glu Leu Ile Lys Thr Val Thr Glu Ala His Val Ala Thr Asn Ala
             20                  25                  30
Gln Gly Ser His Trp Lys Gln Lys Arg Lys Phe Leu Pro Glu Asp Ile
         35                  40                  45
Gly Gln Ala Pro Ile Val Asn Ala Pro Glu Gly Gly Lys Val Asp Leu
     50                  55                  60
Glu Ala Phe Ser His Phe Thr Lys Ile Ile Thr Pro Ala Ile Thr Arg
 65                  70                  75                  80
Val Val Asp Phe Ala Lys Lys Leu Pro Met Phe Cys Glu Leu Pro Cys
                 85                  90                  95
Glu Asp Gln Ile Ile Leu Leu Lys Gly Cys Cys Met Glu Ile Met Ser
            100                 105                 110
Leu Arg Ala Ala Val Arg Tyr Asp Pro Glu Ser Glu Thr Leu Thr Leu
        115                 120                 125
Asn Gly Glu Met Ala Val Thr Arg Gly Gln Leu Lys Asn Gly Gly Leu
    130                 135                 140
Gly Val Val Ser Asp Ala Ile Phe Asp Leu Gly Met Ser Leu Ser Ser
145                 150                 155                 160
Phe Asn Leu Asp Asp Thr Glu Val Ala Leu Leu Gln Ala Val Leu Leu
                165                 170                 175
Met Ser Ser Asp Arg Pro Gly Leu Ala Cys Val Glu Arg Ile Glu Lys
            180                 185                 190
Tyr Gln Asp Ser Phe Leu Leu Ala Phe Glu His Tyr Ile Asn Tyr Arg
        195                 200                 205
Lys His His Val Thr His Phe Trp Pro Lys Leu Leu Met Lys Val Thr
    210                 215                 220
Asp Leu Arg Met Ile Gly Ala Cys His Ala Ser Arg Phe Leu His Met
225                 230                 235                 240
Lys Val Glu Cys Pro Thr Glu Leu Phe Pro Pro Leu Phe Leu Glu Val
                245                 250                 255
Phe Glu Asp

<210> SEQ ID NO 2
<211> LENGTH: 780
<212> TYPE: DNA
<213> ORGANISM: Homo sapiens

<400> SEQUENCE: 2
gagctgcaga agtccatcgg gcacaagcca gagcccacag acgaggaatg ggagctcatc      60
aaaactgtca ccgaagccca tgtggcgacc aacgcccaag cagccactg gaagcaaaaa     120
cggaaattcc tgccagaaga cattggacaa gcaccaatag tcaatgcccc agaaggtgga     180
aaggttgact ggaagccttt cagccatttt acaaaaatca tcacaccagc aattaccaga     240
gtggtggatt ttgccaaaaa gttgcctatg ttttgtgagc tgccatgtga agaccagatc     300
atcctcctca aggctgctg catggagatc atgtcccttc gcgctgctgt gcgctatgac     360
ccagaaagtg agactttaac cttgaatggg gaaatggcag tgacacgggg ccagctgaaa     420
aatgggggtc ttggggtggt gtcagacgcc atctttgacc tgggcatgtc tctgtcttct     480
ttcaacctgg atgacactga agtagccctc cttcaggccg tcctgctgat gtcttcagat     540
cgcccggggc ttgcctgtgt tgagagaata gaaaagtacc aagatagttt cctgctggcc     600
tttgaacact atatcaatta ccgaaaacac cacgtgacac acttttggcc aaaactcctg     660
atgaaggtga cagatctgcg gatgatagga gcctgccatg ccagccgctt cctgcacatg     720
```

```
aaggtggaat gccccacaga actcttcccc cctttgttct tggaagtgtt cgaggattag    780
```